United States Patent
Uehara

(10) Patent No.: US 11,317,824 B1
(45) Date of Patent: May 3, 2022

(54) SYSTEM AND METHOD FOR IDENTIFYING BREATHING PATTERNS DURING RUNNING AND OTHER APPLICATIONS

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 467 days.

(21) Appl. No.: 15/492,973

(22) Filed: Apr. 20, 2017

Related U.S. Application Data

(63) Continuation-in-part of application No. 14/789,136, filed on Jul. 1, 2015, now Pat. No. 9,706,962, which is a continuation-in-part of application No. 14/132,808, filed on Dec. 18, 2013, now Pat. No. 9,226,706.

(60) Provisional application No. 62/325,196, filed on Apr. 20, 2016, provisional application No. 62/019,522, filed on Jul. 1, 2014, provisional application No. 61/739,160, filed on Dec. 19, 2012.

(51) Int. Cl.
| | |
|---|---|
| *A61B 5/08* | (2006.01) |
| *A61B 5/024* | (2006.01) |
| *A61B 5/00* | (2006.01) |
| *A61B 5/11* | (2006.01) |
| *A63B 23/18* | (2006.01) |
| *A63B 71/06* | (2006.01) |
| *A63B 24/00* | (2006.01) |

(52) U.S. Cl.
CPC ........ *A61B 5/0816* (2013.01); *A61B 5/02438* (2013.01); *A61B 5/0803* (2013.01); *A61B 5/6831* (2013.01); *A61B 5/7278* (2013.01); *A61B 5/742* (2013.01); *A61B 5/112* (2013.01); *A61B 5/1123* (2013.01); *A61B 2560/0214* (2013.01); *A63B 23/185* (2013.01); *A63B 24/00* (2013.01); *A63B 71/0619* (2013.01); *A63B 71/0686* (2013.01); *A63B 2230/40* (2013.01)

(58) Field of Classification Search
CPC ..... A61B 5/0816; A61B 5/6831; A61B 5/112; A61B 5/1123; A63B 2230/40; A63B 23/185; A63B 71/0619; A63B 71/0686; A63B 24/00; G01C 22/006
See application file for complete search history.

(56) References Cited

U.S. PATENT DOCUMENTS

| | | | |
|---|---|---|---|
| 2007/0173378 A1* | 7/2007 | Jamsen | A61B 5/1123 482/8 |
| 2010/0083968 A1* | 4/2010 | Wondka | A61M 16/12 128/204.23 |
| 2010/0160118 A1* | 6/2010 | Shirasaki | A61B 5/0816 482/13 |

(Continued)

*Primary Examiner* — Puya Agahi
(74) *Attorney, Agent, or Firm* — Staniford Tomita LLP

(57) ABSTRACT

A wearable device and system has been developed to help users learn the practices of diaphragmatic breathing and breathing patterns to improve running and walking performance. The wearable has a breathing sensor (breathe in-breathe out) and a movement sensor used to identify foot strikes. A processor computes the number of foot strikes occurring while inhaling and the number of foot strikes occurring while exhaling to report breathing patterns as a function of time. The algorithms may be modified to teach breathing patterns to athletes in other sports and deep breathing for numerous movement and minimal movement applications.

10 Claims, 15 Drawing Sheets

(56) References Cited

U.S. PATENT DOCUMENTS

2012/0116719 A1* 5/2012 Takahashi ............ A61B 5/1112
702/160

* cited by examiner

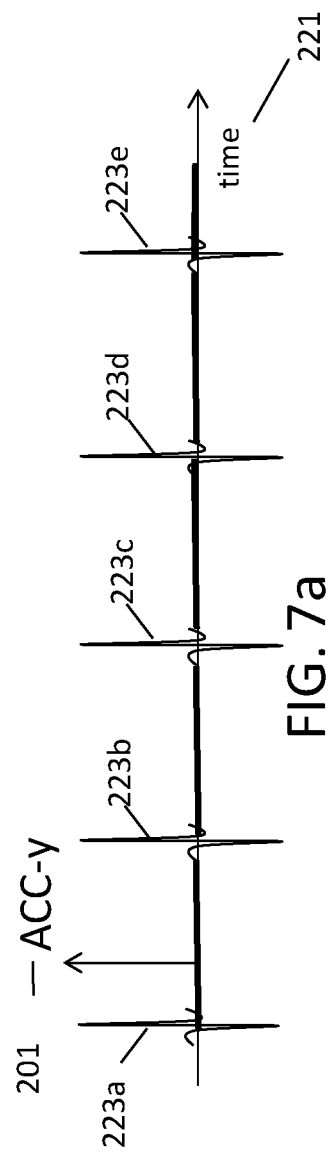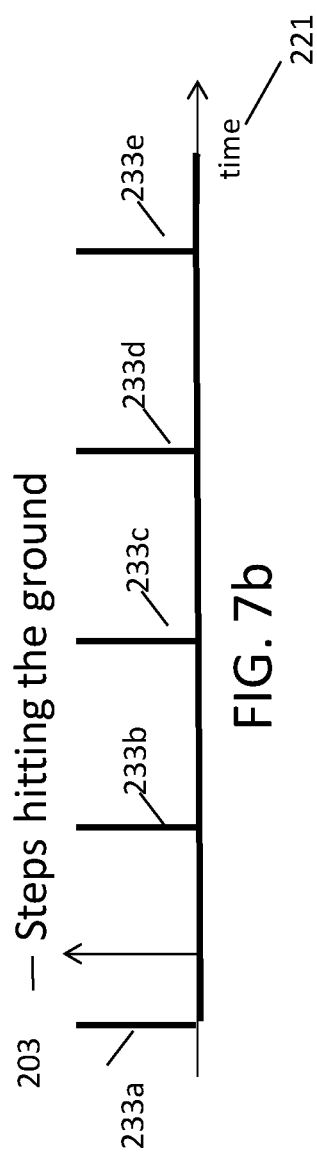

SYSTEM AND METHOD FOR IDENTIFYING BREATHING PATTERNS DURING RUNNING AND OTHER APPLICATIONS

CROSS-REFERENCE TO RELATED APPLICATIONS

This application also claims priority to U.S. Provisional Application No. 62/325,196, entitled "System And Method For Identifying Breathing Patterns During Running And Other Applications", filed Apr. 20, 2016. This application is also a continuation in part of U.S. patent application Ser. No. 14/789,136, entitled "Apparatus And Method For Teaching And Algorithms For Identifying Qualifying Movements", filed Jul. 1, 2015, which claims priority from U.S. Provisional Application No. 62/019,522, entitled "Apparatus And Method For Teaching And Algorithms For Identifying Qualifying Movements", filed Jul. 1, 2015. U.S. patent application Ser. No. 14/789,136 is a continuation in part of U.S. patent application Ser. No. 14/132,808, entitled "System, Apparatus, And Method For Promoting Usage Of Core Muscles And Other Applications", filed Dec. 18, 2013, now U.S. Pat. No. 9,226,706 which claims priority to U.S. Provisional Application No. 61/739,160, entitled "System For Promoting Usage Of Core Muscles And Other Applications", filed Dec. 19, 2012. The disclosures of U.S. patent application Ser. Nos. 14/132,808, 14/789,136, 61/739,160, 62/019,522, and 62/325,196 are hereby incorporated herein by reference in their entirety. The aforementioned patent references are referred to as "Incorporated Patent References."

FIELD OF THE INVENTION

Embodiments disclosed relate to systems and methods for development of breathing patterns coordinated with foot strikes and diaphragmatic breathing for walkers and runners. Embodiments also relate to systems and methods for development of breathing patterns coordinated with body movements for other sports such as cycling, canoe paddling, and swimming. Embodiments further relate to systems and methods for development of breathing patterns and habits in the practice of yoga, meditation, and other practices where deep breathing is emphasized and carefully monitored and controlled. Embodiments relate to apparatus, systems, and methods for identifying when a user is breathing in (inhaling) or breathing out (exhaling) and when the user begins to breathe in and breathe out relative to foot strikes in the case of running or walking, or other measurable body movements in other activities.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include but are not limited to sensors such as accelerometers, gyros, magnetometers, altimeters, force, and/or pressure sensors. Examples of such devices include smart phones, cell phones, gaming devices, and wearable devices or "wearables." A large number of wearables target health and fitness applications where steps taken and flights of stairs taken by device users are tracked utilizing accelerometers and altimeters. Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track.

Running and walking are sports and pastimes that may benefit from the use of optimized wearable devices. Speed, distance, and heart rate are parameters that are already monitored and tracked during running and walking using currently available wearables. Breathing is a critical activity which bringing oxygen to the body and eliminating carbon dioxide. From short distance running events such as the 100 meter dash to long distance events like a marathon and beyond, as well as casual short and long walks for exercise, optimizing or improving breathing may be important to both achieve optimum performance and reduce injuries. While there are wearable devices to monitor and provide feedback for many important parameters, there are no known consumer devices to monitor and provide feedback regarding breathing for runners, walkers, and other athletes such as cyclists, swimmers, canoe paddlers, those in rowing sports, as well as those in sports involving a lot of running such as basketball, football, and soccer.

Two critical aspects regarding breathing include the primary driving mechanism for moving air into and out of the lungs, and breathing patterns of inhale and exhale and if and how they are coordinated with foot strikes (steps).

There are two predominant ways for people to breathe. First, is chest breathing, where the chest area and rib cage in the upper torso expands as air is breathed in and the chest area and rib cage contracts as the air is breathed out. Second, is diaphragmatic breathing, where breathing is performed while contracting the diaphragm. In diaphragmatic breathing, air enters the lungs and the lower abdominal section expands as air is breathed in and the abdominal section contracts as air is breathed out. Diaphragmatic breathing is also known as diaphragmatic breathing, abdominal breathing, or deep breathing. Diaphragmatic breathing is believed to be beneficial both during periods of relaxation and meditation, and athletic activity. Diaphragmatic breathing may allow more air to move into and out of the lungs than chest breathing.

During each step during running, the force on the body via a foot striking the ground may exceed twice the body weight. On each exhale, the diaphragm and muscles around the core relax, reducing core stability. As a result, this may cause each step occurring together and simultaneously with an exhale to have a greater negative impact on the body. Most runners either breathe in an ad hoc manner with no specific pattern, or with an even count cadence meaning if they breathe in for two steps, they breathe out for two steps where the total count is four which is an even number. In the case of an even count cadence, the result is each exhale occurs with the same foot (left or right foot) striking the ground. Some have found that this can result in eventual pain or injury on the side of the body which strikes the ground coincident with the start of each exhale, when the same side of the body repetitively strikes on the exhale over the course of long runs. One approach that has been proposed to reduce the impact of this is to breathe with an odd count cadence. For example, a runner may breathe in for three counts and out for two for a 3/2 breathing pattern.

Alternatively, the runner may breathe in for two counts and out for one for a 2/1 breathing pattern. By alternating the foot that strikes the ground at the start of each exhale from left to right, the result may be less accumulated wear and tear on the body. An additional benefit may be that the runner inhales for a longer period of time than the runner exhales, which may result in more core support throughout the run since there may be greater core support during an inhale. Breathing with a specific pattern may be referred to as rhythmic breathing. In rhythmic breathing, different count cadences may be desirable during different parts of a run. The count cadence may be an additional component in a runners training and racing strategy.

In addition to bringing oxygen into the body, effective breathing removes carbon dioxide ($CO_2$) from the lungs. Heavy exercise generates $CO_2$ in muscle that is returned to the lungs by the blood and removed during exhale. While it is important to remove $CO_2$, if $CO_2$ is being removed at a rate faster than it is being generated, it may cause hyperventilation and can result in dizziness. As a result, a balance is desired between oxygen intake and $CO_2$ removal and the preferred rhythmic breathing pattern will likely change during the course of a run—particularly as the athlete fatigues.

In summary, the use of the combination of diaphragmatic breathing and rhythmic breathing (rhythmic diaphragmatic breathing) can improve the delivery of oxygen to the body, removal of $CO_2$ from the lungs, and possibly reduce impact on the body during strides which can have an accumulating impact over long training sessions and runs. Rhythmic diaphragmatic breathing can be beneficial in training and racing in sprints to long runs such as marathons and beyond. In cycling, running steps may be replaced by pedal strokes and an odd count cadence may be used. In a similar manner, the concepts of diaphragmatic breathing and rhythmic breathing may be applied to other sports and repetitive activities where speed and endurance are important.

What is needed is a convenient, low cost wearable device that can be used to teach, train, monitor, and track breathing patterns and breathing style in non-movement, minimal movement, and athletic activities including running, walking, and sports involving running, and can be beneficial to increase well-being, improve performance, and may reduce injuries.

SUMMARY OF THE INVENTION

A wearable device and system are designed to provide immediate feedback and tracking to a user to improve breathing techniques and the learning and improvement of breathing patterns in non-movement and athletic activities such as running and walking. The wearable contains a breathe in-breathe out sensor that may track when a user begins breathing in up until the point in time when the user begins breathing out, and when the user begins breathing out up until the point in time when the user begins breathing in. Further, the wearable may contain a movement sensor to identify when the user takes a step when running or walking. A processor may combine the signals from the breathe in-breathe out sensor and the movement sensor to determine rhythmic breathing patterns and provide immediate feedback and data tracking to a user. This data may be used to improve performance, may reduce injuries during running and walking and other activities and sports, and provide additional data to improve training and racing strategies. The data made available to the user may be combined with other data including pace (minutes per mile), distance, location, and heart rate as a training and improvement tracking tool.

When inhaling while performing diaphragmatic breathing, the region of the front torso over the celiac plexus tends to move outward. This region is often referred to as the celiac plexus or the solar plexus. When exhaling, the celiac plexus tends to move inward. Due to the movement of this region during diaphragmatic breathing, it is an effective location for a wearable device to detect this movement. In an embodiment, the wearable device may detect this movement using movement sensors to identify when the user is performing breathe in-breathe out. However, if the user is also moving, body movements may be difficult to distinguish from diaphragmatic breathing. In an embodiment, the breathe in-breathe out sensor is a force or pressure sensor and is placed over this region near the lower part of the solar plexus and held in place with a belt that may be elastic or partially elastic. When inhaling using diaphragmatic breathing, the pressure on the wearable placed over this region of the celiac plexus will increase and when they exhale it will decrease. A number of sensing technologies may be used in the implementation of the breathe in-breather out sensor including include strain gage, capacitive, force resistive, magnetic, optical, and piezoelectric.

Other locations may be suitable for the wearable device to detect breathe in-breathe out. The region below the ribs and above the waist on the front and sides of the body that may move outward or firm during an inhale and move inward or soften during an exhale. More specifically, the area beneath the left or right ribs, or on the sides of the body may be effective for sensing breathe in-breathe out.

The movement sensing technology used for movement sensing may depend on the application and the movement to be identified. In the application of identifying steps of a runner or walker, an accelerometer may be used to detect steps. Gyros and other sensor technologies may also be used. In an embodiment, more than one sensor technology may be used to identify a user's steps.

In order to identify a rhythmic breathing pattern, the breathe in-breathe out sensor output after filtering may resemble a triangular wave where the rise and fall slopes may differ, depending upon the breathing pattern. When accelerometers are used to implement the movement sensor to detect steps, the accelerometer output on the axis aligned with gravity may be amplified and hard-limited to result in impulses at or near the moments of running or walking steps. The roughly triangular wave from the breathe in-breath out sensor and the impulses from the movement sensor corresponding to steps can be processed by Digital Signal Processing (DSP) algorithms to identify an estimate of the number of steps taken during the inhale and the number of steps taken during the exhale of the user. This information can be available moments after a full cycle of breathe in and breathe out is complete. This information can be reported immediately via the device, an app running on a smart device such as a smart pad or smart watch or other portable device, or recorded for later recall with other parameters taken during a run or walk. If the device includes a display, the pattern can be shown immediately on the display.

The device and system may be applied to other sports including cycling. In cycling, the up and down movement of the torso may not be as pronounced as for a runner. Instead, left to right rocking of the torso may be more pronounced as a cyclist peddles the bicycle. Let the z-dimension be in the direction a cyclist is moving. Each 360 degree rotation of a foot on a pedal may have a corresponding left and right torso rotation about the z-axis. Alternatively, let the y-dimension be in the direction of gravity (up and down). Each 360 degree rotation of a foot on a pedal may have a corresponding complete left to right and back to left torso rotation about the y-axis. In some cases there will be both rotational elements present that may be detected. In the case of cycling, starting from the 6 o'clock position with one leg fully extended, 360 degree pedal rotations per breath in and 360 degree peddle rotations per breath out may be one relevant rhythmic breathing pattern to monitor. This illustrates how the inventive concepts may be applied to other another sports. Similar extensions are possible for other sports and applications.

In specific running sports like hurdles, the coordination of breathing patterns with steps between hurdles may improve performance. It is desirable for the hurdler to have a specific number of steps between each hurdle. It may also be desirable to coordinate this with a specific number of breathes between and through each hurdle. The device and system may be used to track and improve breathing for hurdlers via increasing consistency.

By encouraging the more effective diaphragmatic breathing over chest breathing, and increasing consistent breathing patterns with athletic movements, the device and system may be beneficial to athletes in different sports.

For some sports and applications, the amount of air needed to be breathed in and out may change as an event progresses. A breathing monitor may measure both the pattern of breathing and the relative amount the abdomen may expand and compress with each breath during an event. This may allow an athlete or coach to further optimize and fine tune breathing strategy. Swimming is an example of a sport where monitoring breathing along with body rotation and movement may be beneficial. Since most athletes will tend to breathe less deeply with higher frequency as an event progresses, as well as change their movement patterns as they tire, being able to monitor these parameters can be very helpful for both athletes, coaches, and trainers. The inventive device and system may be optimized to provide such data for performance improvement.

In different sports and applications, it may be valuable to focus on rhythmic breathing during certain portions of an event and allow more ad hoc breathing during other portions of an event. Location and time tracking data may be combined with heart rate tracking and breathing patterns to get a more comprehensive view of what the athlete is doing and when.

Chronic Obstructive Pulmonary Disease (COPD) is an umbrella term used to describe progressive lung diseases including emphysema, chronic bronchitis, refractory (non-reversible) asthma, and some forms of bronchiectasis. COPD is characterized by increasing breathlessness. It has been suggested that diaphragmatic breathing can be a useful component in managing COPD.

In an embodiment, the system utilizes a movement sensor to generate step impulses from accelerometer transients created when a runner or walker steps. A breathe in-breathe out sensor, responsive to a user's diaphragmatic breathing may generate signals identifying when the user is inhaling and when the user is exhaling. In an embodiment, the breathe in-breathe out sensor identifies when the start of inhale begins and the start of exhale begins. The breathe in-breathe out signal and the step impulse signal may be used together to count the number of running steps during the inhale, and the number of running steps during the exhale. These counts may be immediately reported to the user or stored for reporting to the user at a later time to promote diaphragmatic breathing and the practice of utilizing breathing patterns.

In an embodiment, the step impulse signal may be delayed by a smart delay to make the counting robust to time perturbations of the breathing derived and step derived signals.

In an embodiment, the wearable device described in the Incorporated Patent References to promote core contraction sensing and qualifying movement protection may be used to implement the wearable device and system.

In an embodiment, a force sensing resistor or a pressure sensor may be utilized to implement the breathe in-breathe out sensor.

In an embodiment, an accelerometer, gyro, or other sensor technology may be used separately or together to implement the movement sensor for detecting running or walking steps.

In another embodiment, step impulses may be generated by processing the accelerometer output including utilizing hard-limiting.

In an embodiment, the number of hip rotations during inhale and the number of hip rotations during exhale may be measured and reported by the wearable and system.

In an embodiment, movement sensors may be used to determine approximately the moments in time a running event starts and when it ends. This may be used to "time crop" the data to focus on the relevant times when a running event is on-going.

In different embodiments, the inventive system can communicate data to a mobile computing device, which can be a smart phone, a tablet, a smart watch, or a dedicated computing device. Since smart watches today track heart rate, speed, and distance of a runner, the addition of breathing patterns may complement the already available data for further performance and health improvement.

In an embodiment, the wearable device may communicate to the smart watch or smart device via low energy wireless protocols such as Bluetooth Low Energy or ANT. Other wireless protocols, proprietary wireless protocols, or wired protocols may be used.

In an embodiment, the data may be stored in memory on the wearable device or in the other device and be observed both during and after the run. In an embodiment, breathing patterns may be observed together with other performance metrics such as speed, heart rate, and core muscle usage.

In an embodiment, the wearable may integrate GPS to calculate a user's position with time and a user's speed with time and position.

In an embodiment, the wearable may integrate a heart rate monitor.

In an embodiment, the wearable may by used together with an app or program to promote effective breathing together with a oximeter that measures oxygen carried in the body.

In an embodiment, the wearable may be used together with an app or program to promote use and strengthening of the diaphragm for general wellness and to help manage living with health conditions such as COPD.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 7a illustrates the y-dimension accelerometer data showing transients the result from foot strikes to the ground due to the runner running.

FIG. 7b illustrates accelerometer data from FIG. 18b translated to impulses at time instances that the foot strikes occur.

DETAILED DESCRIPTION

Breathing is a critical element in athletics and especially important in speed and endurance sports like sprinting, hurdles, distance running, speed walking, bicycling, swimming, as well as sports where there is a lot of running or endurance activity involved such as football, basketball, soccer, rugby, and water polo. There are at least two aspects of breathing that are particularly critical: the first is diaphragmatic breathing where the abdominal section expands and contracts during each inhale and exhale, maintaining a high degree of oxygen distribution to the circulatory system and efficient $CO_2$ removal due to deep breaths in and out; and the second is breathing patterns where for example in the case of running, an athlete either breathes with the patterns of: a. ad hoc—where the runner breathes with no particular pattern; b. equal cadence where the runner breathes in or inhales for a certain number of steps and breathes out for the same number of steps; or c. unequal cadence where the runner breathes in for a certain number of steps and breathes out for a different number of steps. Equal cadence and unequal cadence breathing patterns are sometimes referred to as rhythmic breathing patterns. Some have proposed that unequal cadence with an odd number of total steps in the breathe in-breathe out cycle may have advantages such as making the athlete less prone to injury; and if the inhale count exceeds the exhale count, may have the additional advantage of having core muscle support for a longer period of time over the course of the event.

In Incorporated Patent References, a system is described including a wearable device which monitors a user's core muscles and body movements. The system promotes usage of the core muscles in coordination with body movements for back pain rehab and prevention in every day movements and athletic movements. In described embodiments, the core muscles are monitored by a core contraction sensor which may detect firmness change in regions over the core muscles when the muscles are contracted. In these embodiments, force or pressure sensors may be used.

Figure 1:
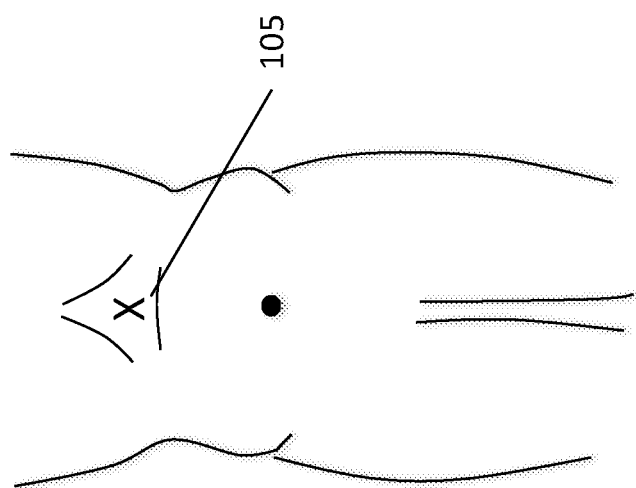
FIG. 1 illustrates the location of the lower part of the celiac plexus or solar plexus.

The celiac plexus or solar plexus, as it is more widely known, is a network of nerves located in the abdomen under the diaphragm near the front of the spine. With reference to FIG. 1, the soft triangular region below the location where the ribs meet marked by the X 105 is a region over the celiac plexus. This region is often loosely referred to as the celiac plexus or the solar plexus. When a person is utilizing diaphragmatic breathing, the region near the X 105 firms due to contraction of the diaphragm and may move outward. The core sensor described in the Incorporated Patent References may detect firmness changes in the core muscles and may be utilized to implement the breathe in-breathe out sensor. The region X 105 is one of many locations that may be suitable to identify contraction of the diaphragm. In this description, the celiac plexus will generally be used but other suitable locations around the front and side abdominal regions may also be effective for breathe in-breathe out sensing.

The Incorporated Patent References describe different methods and techniques to couple the pressure or force sensor to the core muscles in the wearable device. The methods and techniques for coupling the pressure or force sensor to the core muscles to detect a core contraction may be used for coupling the pressure or force sensor to the appropriate body locations such as the celiac plexus to detect breathe in-breathe out of the user. The diaphragm plays a pivotal role in diaphragmatic breathing. The diaphragm is considered one of the inner core muscles. As it contracts, other core muscles may co-contract resulting in both an increase in the volume of the abdominal area, and a firming of at least some of the abdominal muscles. And therefore, in some applications, it may be suitable to use EMG or backscattering techniques described in Incorporated Patent References for breathe in-breathe out sensing.

The wearable device may be connected via a communication technology such as a wireless technology or protocol like Bluetooth or ANT to a smart device, PC, or other dedicated device. Once data is obtained by the breathe in-breathe out sensor, the data may be processed by algorithms that may be performed on a processor and feedback may be provided from the device via a buzzer, speaker, or other sound generator; or an app running on a smart device, PC, or other dedicated device. The app may run on the iOS or android operating system, or it may run on a proprietary operating system. The user may be directed by a voice, coach, music, games, video, or other audio teaching through a program or app. Feedback may be interactive, depending on the data received from the device attached to the user. Feedback may be provided in real-time or after an event. The focus of the programs or apps may include connecting with, developing, exercising, and practicing the use of the diaphragm.

The data provided from monitoring breathing patterns may be included as part of a teaching and practice app to develop and improve breathing skills that may improve the distribution of oxygen to the body and a critical element in wellness activities. The breathing patterns may be combined with monitoring foot strikes or steps during running and even walking. Breathing patterns may also be combined with monitoring torso rotations that may provide a measurement to detect foot rotations on a bicycle. Breathing patterns in water sports such as swimming may also be monitored, again by monitoring torso rotations. These examples may illustrate that the device and system may be useful for sports and activities in addition to running and walking to teach diaphragmatic breathing and breathing patterns. Most generally, the device and system may be used to develop the habit and practice of diaphragmatic breathing and coordination between diaphragmatic breathing and body movements for different applications where diaphragmatic breathing may be utilized. Furthermore via apps, games, video, audio, teaching, correction, and other means, the device and system may encourage the development of habits to make diaphragmatic breathing natural for the user.

Diaphragmatic breathing performed while the body is not moving or minimally moving such as in yoga or meditation, for wellness, or to aid in the management of diseases such as COPD may be also monitored using the breathe in-breathe out sensor. In these applications, the focus may be on different types of deep breathing approaches but most will involve connecting with, developing, and practicing the use of the diaphragm. In an embodiment, for applications such as yoga or meditation, wellness, or disease management, the device may provide immediate affirming feedback or correction to the user through the program, app, or other feedback mechanism. The device may provide an interactive learning experience for the user by providing feedback from the user's body through the wearable device to the teaching program or app. In response to the feedback, the teaching program or app may make specific corrections or provide specific teaching. The device and system may provide audio feedback, a feedback mechanism common in biofeedback devices today where parameters of an audible signal change with a measured parameter. For example, as the user inhales and the pressure on the breathe in-breathe out sensor increases, the frequency of an audible tone may increase. And as the user exhales and the pressure on the breathe in-breathe out sensor decreases, the frequency of the audible tone may decrease.

Figure 2A:
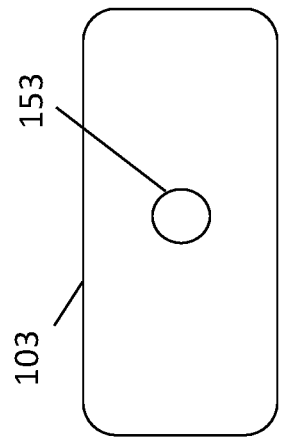
FIG. 2a illustrates a side view of an embodiment of the wearable device and breathe in-breathe out sensor interface.
Figure 2B:
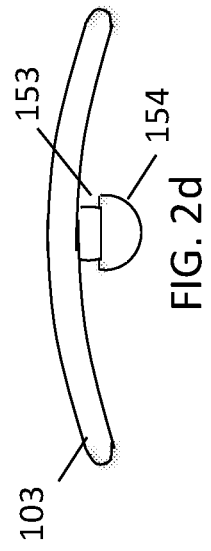
FIG. 2b illustrates a front view of an embodiment of the wearable device and breathe in-breathe out sensor interface.
Figure 2C:
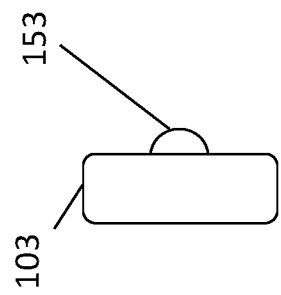
FIG. 2c illustrates a top view of an embodiment of the wearable device and breathe in-breathe out sensor interface showing an internal compartment to house electronics, sensors, and a battery.
Figure 2D:
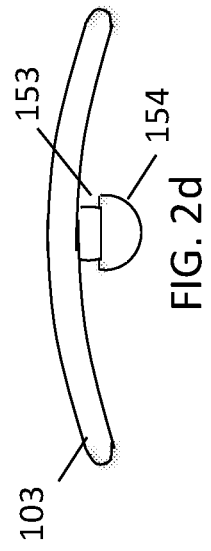
FIG. 2d illustrates a top view of an embodiment of the wearable device with the addition of a bumper.

An example of a system utilizing a force sensor in the form of a force sensing resistor or FSR is shown in FIGS. 2a-2d and will now be examined in more detail. The side view of the device 103 is shown in FIG. 2a. The front view of the device 103 which is the side of the device which may press up against the user's celiac plexus enabling the breathe in-breathe out sensor interface 153 to couple to the user's celiac plexus is shown in FIG. 2b. The top view of the device is shown in FIG. 2c. The device body as shown in FIG. 2c may have varying degrees of curvature in different embodiments. In an embodiment, device 103 may have a bendable structure. In an embodiment of the bendable structure, the device may be substantially continuously bendable. In another embodiment, the device may bend in bendable locations. For example, the device may have three sections and bend in the locations between sections. In another embodiment, there may be no curvature. The device 103 may have a cavity 152 that may include a printed circuit board (PCB) and may contain sensors, a processor, power management electronics, communication electronics, GPS, and a battery.

Figure 2E:
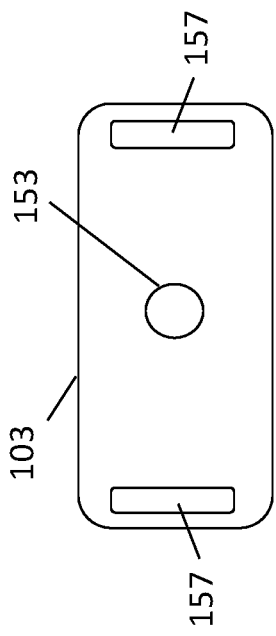
FIG. 2e illustrates a front view of an embodiment of the wearable device and breathe in-breathe out sensor interface.

Some users 101 may have abdominal muscles that are more developed while others may have abdominal muscles that are less developed. Some users may have more body fat over the abdominal muscles and the region of their celiac plexus while others may have less body fat over the abdominal muscles and the region over their celiac plexus. In an embodiment, the sensor interface 153 may extrude from the face of the device 103 and may have an additional member we refer to as a bumper 154 illustrated in FIG. 2d. The bumper may be designed to increase the height and girth of the sensor interface 153. In an embodiment, the bumper may couple to the abdominal section or celiac plexus of the user. In an embodiment, the bumper may have a variable height or girth to accommodate body variations from user to user. The amount of body fat under the sensing area and the amount of abdominal muscle development are examples of body variations. With reference to FIG. 2e, pass through slits 157 may be designed into the device housing to facilitate attachment of the device 103 to a belt.

Figure 3B:
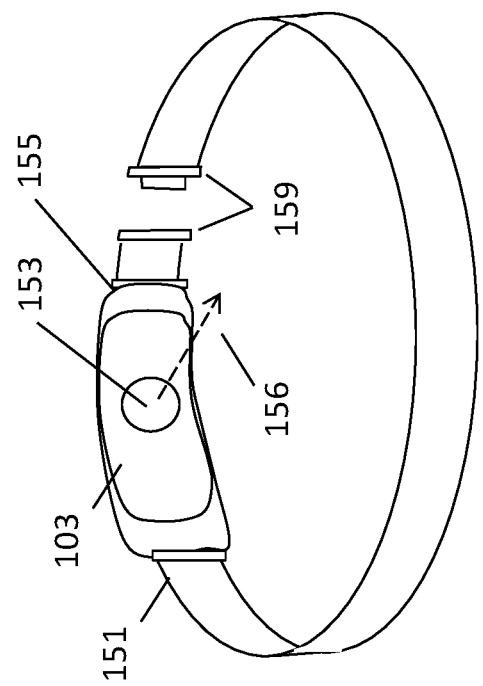
FIG. 3b illustrates an embodiment of a core sensor interface and a wearable device attached to a strap coupled to a belt.
Figure 3A:
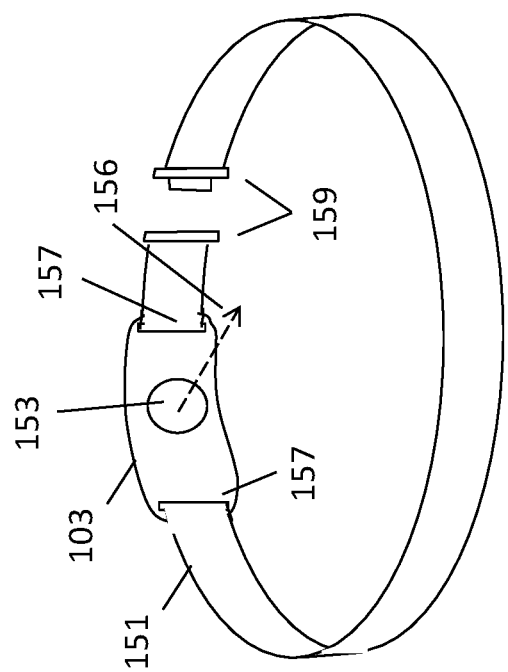
FIG. 3a illustrates an embodiment of a core sensor interface and a wearable device attached to a belt.

With reference to FIGS. 3a and 3b, the breathe in-breathe out sensor interface 153 may couple to the user's 101 celiac plexus or abdominal area in the direction shown by the arrow 156. The belt 151 may be adjustable in length. In an embodiment, the belt 151 may have at least a portion of a length that is elastic. In another embodiment, the belt 151 may be substantially elastic. In another embodiment, the belt 151 may have no portion that is elastic. There are number of ways that the device 103 may connect to the belt 151. Referring to FIG. 3a, the device 103 may have slits 157 in the housing to slip the belt through and attach the device 103 to the belt 151. The belt 151 may connect back to itself after reaching around the user's waist using, for example, magnets, clips, snaps, Velcro, or some other fastener 159. Referring to FIG. 3b, the device 103 may also connect to a strap 155 and the strap 155 may connect to the belt. The strap may be made from a bendable and soft material, or it may be made from a hard material like plastic with bendable elements. Alternatively, the strap may be made out of a combination of materials. For example, the device 103 may snap into a plastic element that is overmolded by a rubber or other bendable material. Many combinations are possible and may be utilized to meet the requirements of different applications.

Figure 4B:
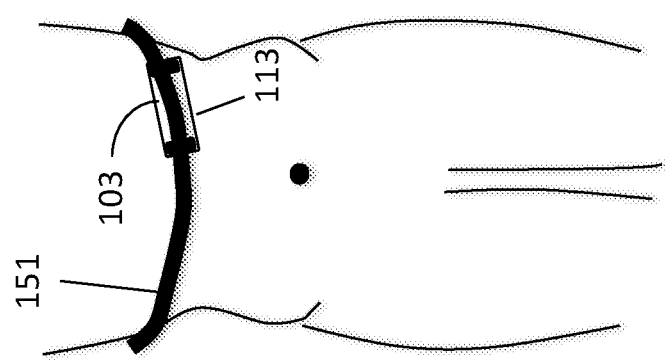
FIGS. 4a, 4b, and 4c illustrate a front view of a user wearing an embodiment of the inventive device worn by a user.
Figure 4A:
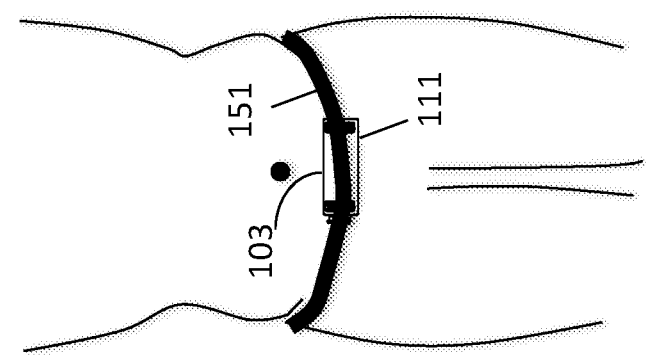
Figure 4D:
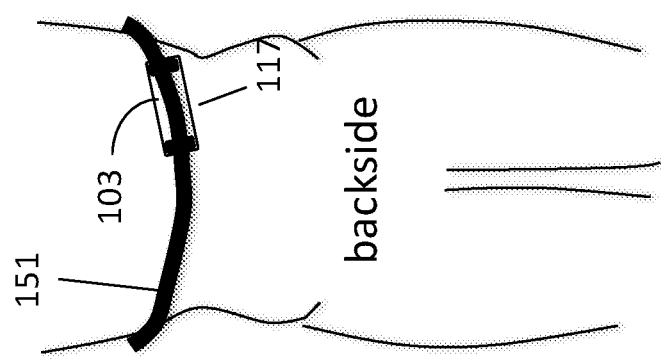
FIG. 4d illustrates a back view of a user wearing an embodiment of the inventive device worn by a user.
Figure 4C:
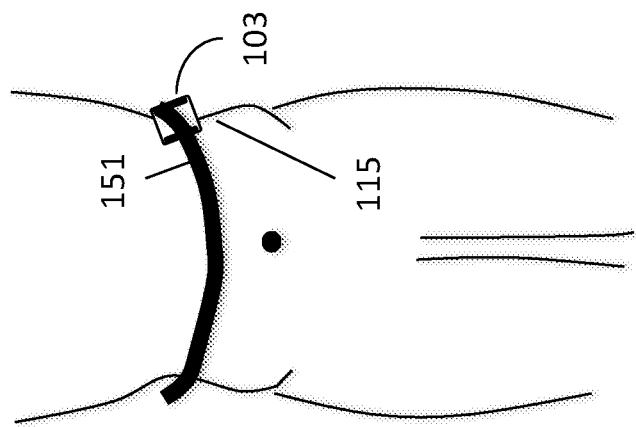

With reference to FIGS. 4a-4d, additional sensing locations to detect breathe in-breathe out of diaphragmatic breathing are illustrated. In FIG. 4a, the wearable device 103 is shown below the navel of the user 111. FIG. 4b illustrates the wearable device 103 below the left ribs of the user 113 and FIG. 4c illustrates wearable device on the side of the user between the ribs and the hip 115. FIG. 4d illustrates the wearable device 103 on the back of the user below the right ribs 117.

Figure 5:
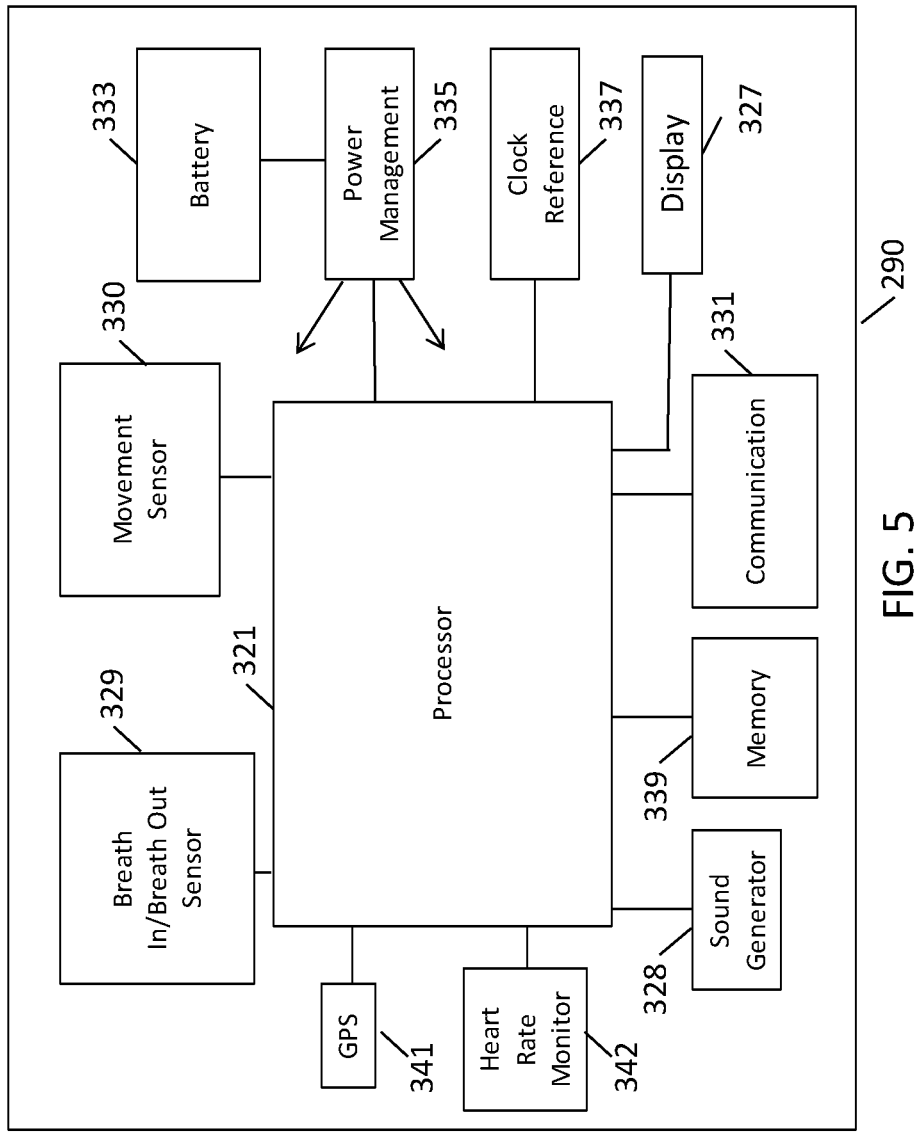
FIG. 5 illustrates a block diagram of then electronics related functional blocks inside the wearable device.

With reference to FIG. 5, a block diagram of an embodiment of the wearable device 290 is illustrated. The processor 321 can also be coupled to various output devices which can provide information to the user which can include one or more of: a sound generator 328 which can emit output signals to the user that indicating the breathe in-breathe out pattern. For example, as the user inhales, the pressure on the wearable breathe in-breathe out sensor may increase. An audible output signal tone generator volume may increase. When the user inhales, the pressure on the breathe in-breathe out sensor may decrease and the audible output signal tone generator volume may decrease. In different embodiments, different output devices can be selected and different feedback signals with appropriate modifications in response to pressure changes may be utilized. For example, a buzzer or sound generator 328 can be useful at home, but these audio output devices may not be appropriate at an office where other employees may hear the output sounds. An output device such as a visual display or monitor 327 may display changing light or other visual output to provide feedback to a user when audible feedback might be disruptive to others.

The processor 321 may also be coupled to a communications device 331 that can transmit information to other devices through a wired or wireless communications connection, for example the communications device 331 may be a Bluetooth device that provides wireless communications with other devices. A battery 333 may be coupled to a power management module 335 which can control the distribution of electrical power to the system components. The battery 333 may be rechargeable and capable of being charged with a charger. The processor 321 may also be coupled to a memory 339 which can record user breathe in-breathe out and movement data. The memory 339 may store or record raw data, partial results, or complete results from the processor 321 executing digital signal processing. The system can also include a clock reference 337 which may provide a system reference clock to the processor which may also be used to derive sampling clocks for the breathe in-breathe-out sensor 329 and the movement sensor 330. If the system has a minimum of intermittent access to date and time information, for example through a cellular system, the clock reference 337 may be utilized in an algorithm using such date and time information so that recorded movements, breathe in-breathe out data, and any other results can be stored with time stamps. Date and time information from the smart device, PC, or other dedicated device may be used to provide date and time information to the device and system. GPS 341 may be included for some applications and can be used to track user location and speed. Heart Rate Monitor 342 technology may be integrated for some applications. A heart rate monitor 342 will generally have elements that are included into the device housing and require some of the elements on the device 103 interface directly to the user's skin.

Figure 6C:
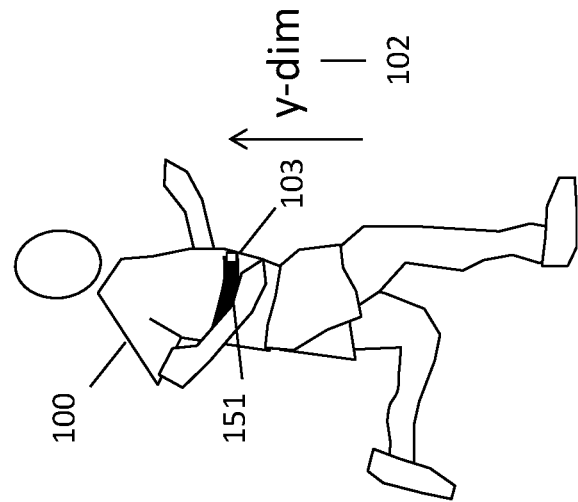
FIG. 6c illustrates a running user wearing the wearable device.
Figure 6B:
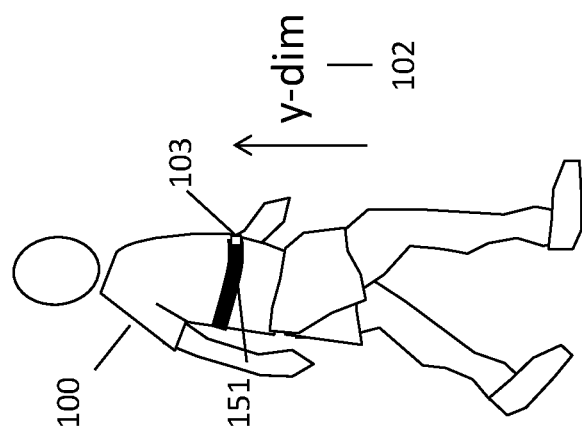
FIG. 6b illustrates a walking user wearing the wearable device.
Figure 6A:
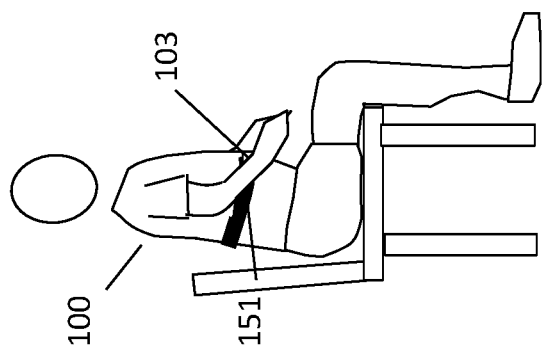
FIG. 6a illustrates a seated user wearing the wearable device.

Referring to FIG. 6a, a depiction of a user 100 in the seated position wearing the wearable device 103 is shown. The seated user 100 may utilize the device 103 as part of a learning system to practice meditation and diaphragmatic breathing. Referring to FIG. 6b, a depiction of a user 100 walking with the y-dimension 102 defined in the up and down direction wearing the wearable device 103. This orientation is used for both the walker in FIG. 6b and the runner in FIG. 6c. If the wearable device 103 is worn over the runner's abdominal section, for example, just beneath the left ribs, as foot strikes occur, the y-dimension accelerometer may show transients similar to those illustrated in FIG. 7a. Each transient corresponds to a step taken by an alternate foot. For example 223a may be a right foot step, 223b may then be a left foot step, and 223c may again be a right foot step and so forth. The location of the steps in time may be translated to impulses as shown FIG. 7b. Amplification or gain and hard-limiting are digital signal processing techniques that may be used to translate step data 223 into impulses 233. The impulses in FIG. 7b identify the time position of foot strikes. In an embodiment, sensor data corresponding to foot strikes are translated to a representation in time similar to the impulses of FIG. 7b. For example foot strike transient 223a has impulse counterpart 233a, foot strike transient 223b has impulse counterpart 233b, and so forth.

In most microprocessor based systems, a system clock is used to clock the processor. In modern day systems, the system clock for the processor may be generated by a phase-lock loop locked to a reference clock and be several mega-Hertz to giga-Hertz in frequency. The system clock may be divided down and used to clock the sample rates of the sensors. Alternatively, the reference clock may be divided down and used to clock the sample rates of the sensors. In some applications, the system clock for the processor may be variable in frequency, depending on the processing requirements. The sensors may be digital, where they require an input clock to operate. They may also be analog and be sampled by an analog-to-digital converter which will utilize an input clock. While the system clock for the processor may be in the mega-Hertz range or much larger, the rate at which sensor data may be acquired may be in the tens of Hertz range up to the kilo-Hertz range.

Common stride rates for recreational runners may be around 150 foot strikes per minute. That corresponds to 5 foot strikes every two seconds. The sensor acquisition clock or sensor clock may be, for example, 30 Hz. At a 30 Hz sensor clock, there would be 60 total tick marks and roughly a step impulse every 12th sensor clock cycle. For many applications, this may be sufficient time resolution for an acceptable user experience. In an embodiment, a higher sensor clock frequency may be used. In another embodiment, a lower sensor clock frequency may be used. Low cost sensors which operate at frequencies much greater than 30 Hz are widely available for athletic and other applications.

Figure 8:
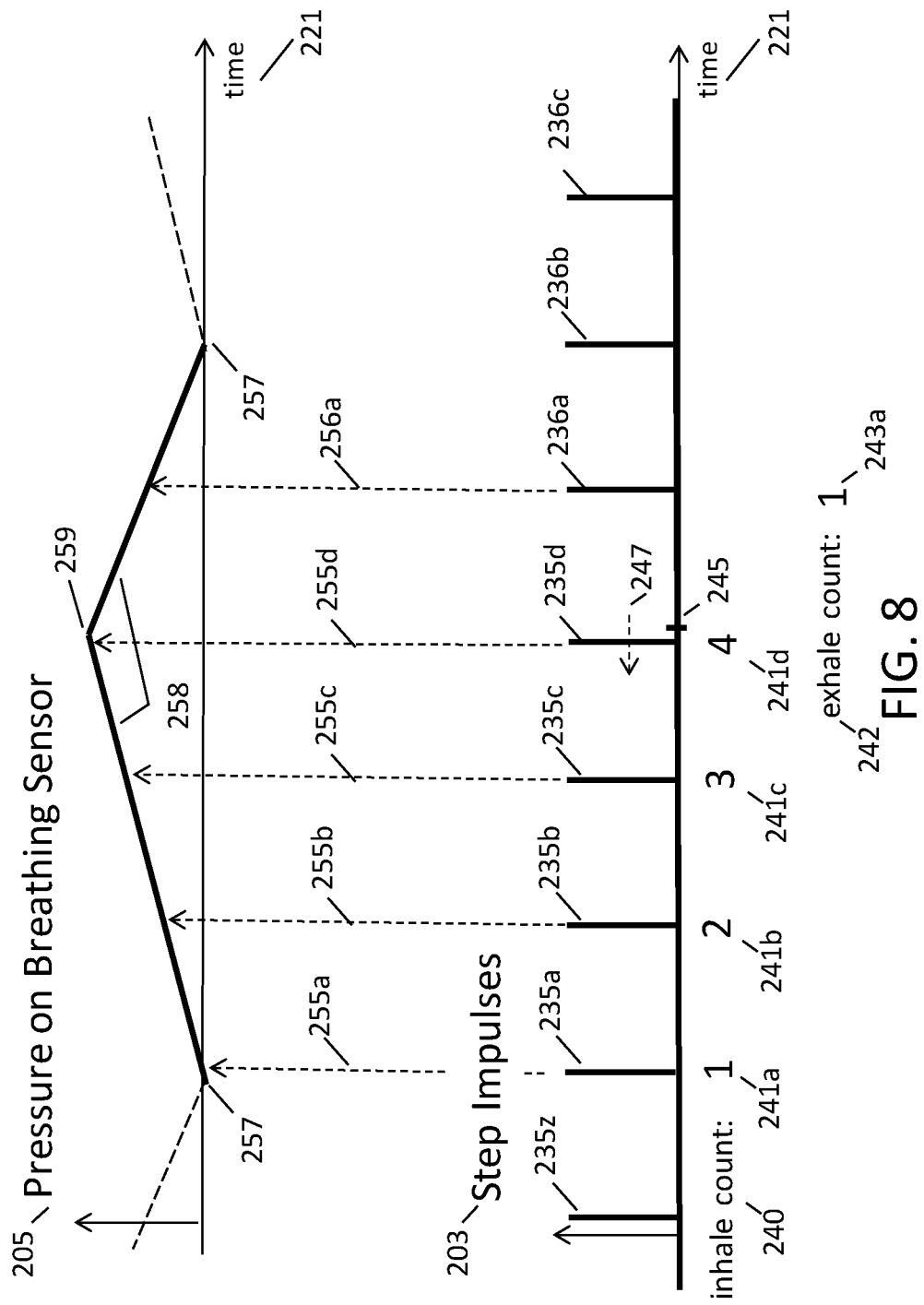
FIG. 8 illustrates breathing sensor data (upper graph) together with the time reference (lower graph) and a simple implementation that may be sensitive to small time perturbations.

Let us examine how the data from the breathe in-breathe out sensor and the movement sensor may be used to identify the breathing pattern of a runner. Referring to FIG. 8, an example of idealized filtered data from the breathing sensor 205 is shown above, and the step impulses 203 are shown below for a 3/2 breathing pattern. The breathing sensor is shown as a roughly periodic triangular signal which may be representative of the breathe in-breathe out sensor output. When the runner inhales, the sensor value begins to rise and maintains a predominantly positive slope. The start of inhale is identified as 257. It may also be considered the end of exhale from the previous breathing cycle. When the runner exhales, the sensor value begins and maintains a predominantly negative slope. The start of exhale is identified as 259. The combination of inhale and exhale comprises one period of a breathe in-breathe out cycle 258. The representation of a straight line with a positive slope corresponding to breathe in and a straight line with a negative slope corresponding to breathe out is simplified. After appropriate filtering of the breathe in-breathe out sensor output, this simple model may be adequate to capture the important aspects of the sensor output.

While both the breathe in-breathe out sensor output 205 and step impulses 203 appear somewhat periodic, small time perturbations due to random changes from cycle to cycle in breathing and running stride may move the start of inhale 257, start of exhale 259, and step impulses 203 by small amounts left or right. This example will illustrate how a small time perturbation may result in an incorrect breathing pattern identification.

Step impulses 235a-235d point to arrows 255a-255d, which point to the inhale portion of one period of the breathe in-breathe out cycle 258. Step impulse 235d was advanced in time due to a perturbation 247 from the correct time position 245. This may result in inhale count 240 counting from 1 through 4 (241a-241d), associated with the breathe in portion of the cycle 258 and a counting error is generated. Step impulse 236a points to arrow 256a, which is the only step impulse associated with the exhale portion of the cycle 258. Exhale count 242 has only a count of 1 243a. The result is this pattern may be identified incorrectly due to the counting error as a 4/1 breathing pattern instead of the correct 3/2 breathing pattern.

Figure 9:
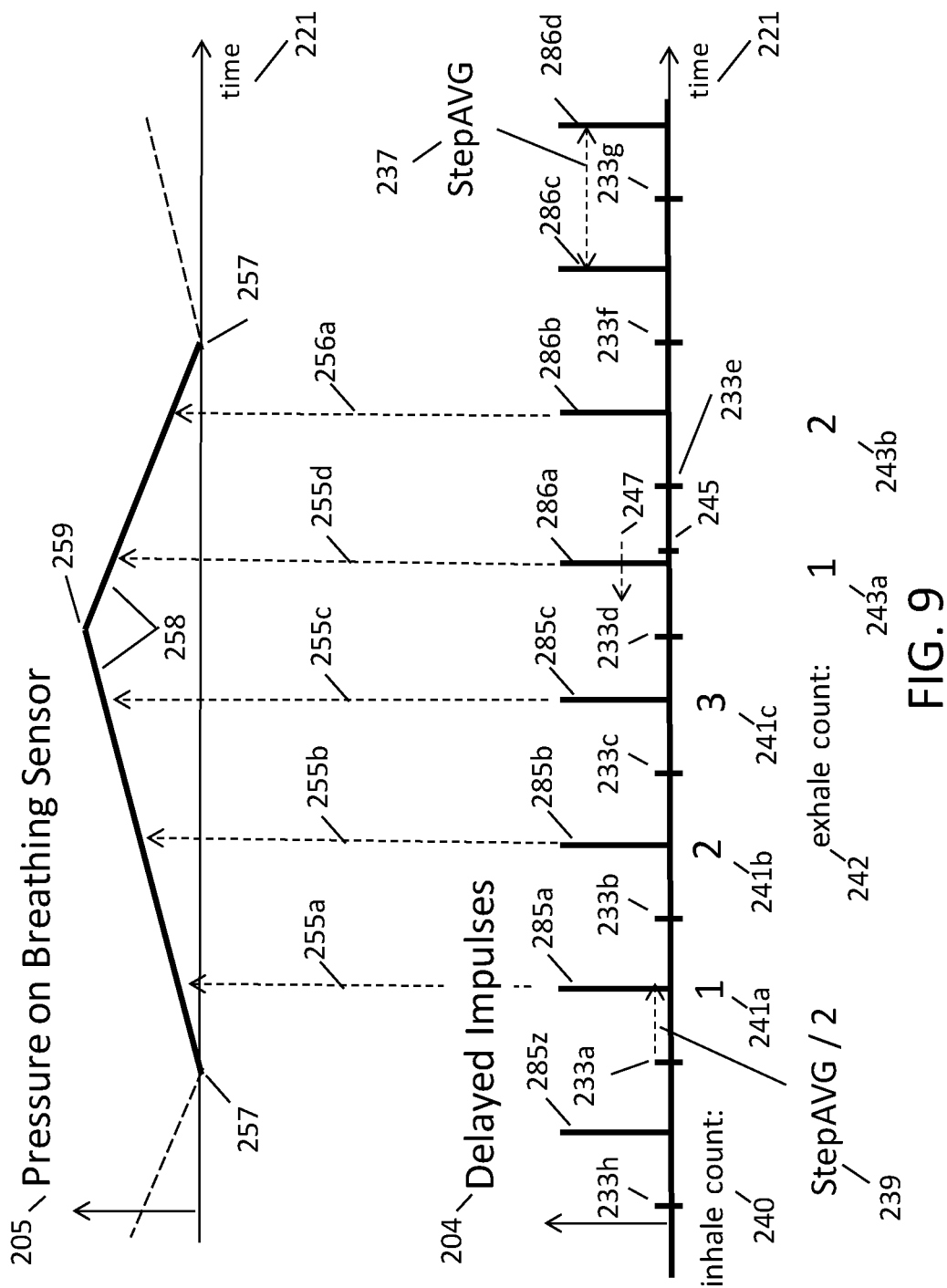
FIG. 9 illustrates breathing sensor data (upper graph) together with the time reference (lower graph) with an implementation that may be robust to small time perturbations.
Figure 10:
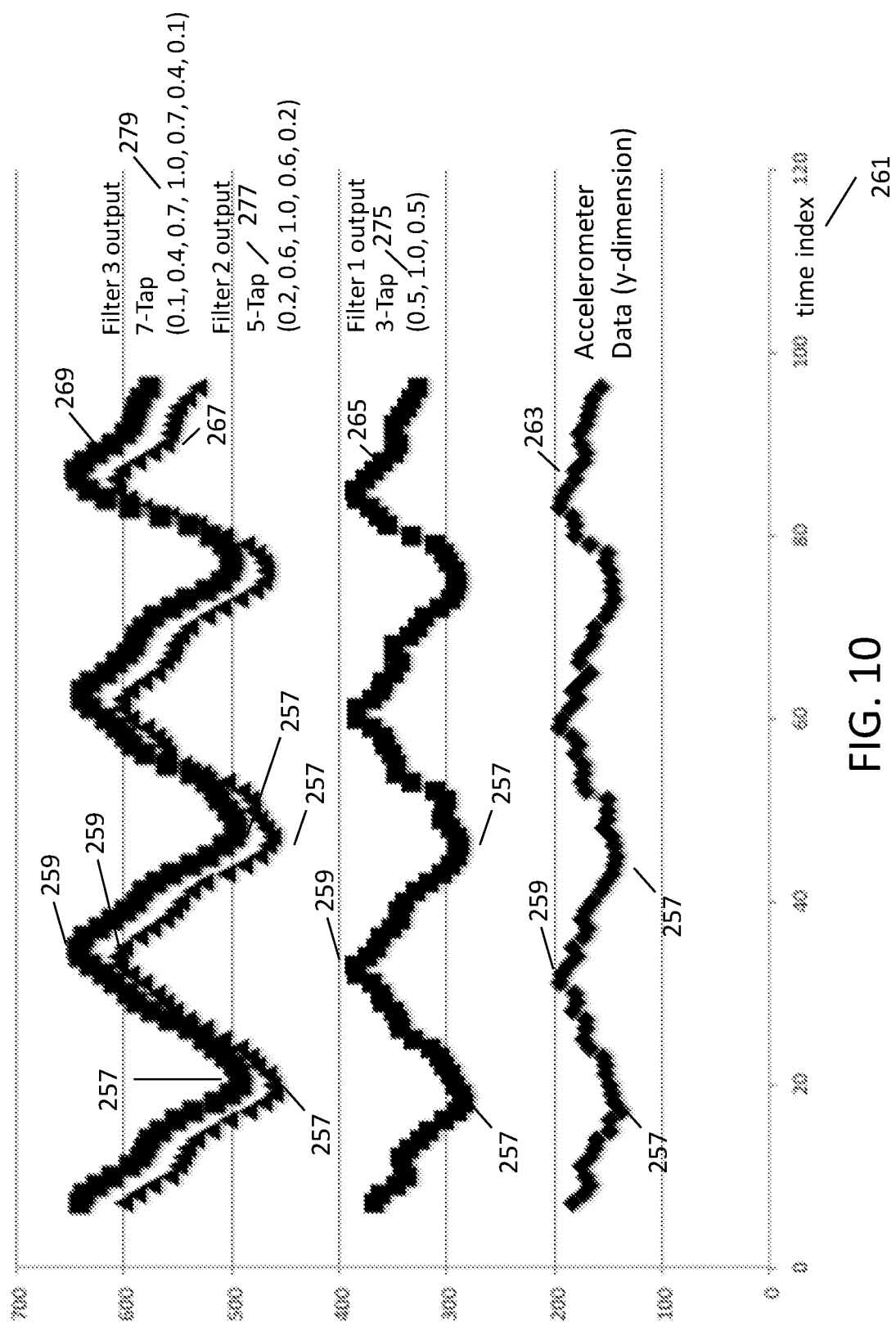
FIG. 10 illustrates breathing sensor data vs. time from a runner wearing the wearable device and filtered versions of the sensor data using different FIR filter tap lengths.

There are a number of approaches that may be taken to achieve robustness to small cycle to cycle time perturbations. One approach is shown in FIG. 9 and uses the principle of a smart delay. Referring to FIG. 10, data from a y-dimension accelerometer from a runner jogging with a 2/2 pattern is shown 263. The output of a 3-tap 265, 5-tap 267, and a 7-tap 269 finite impulse response or FIR filter is shown. In this example, after the 5-tap filter, the output is predominantly monotonic as it transitions from the start of inhale 257 to the start of exhale 259, and then back from the start of exhale 259 to the start of inhale 257. With reference to the 7-tap filter output 269, by identifying the minimum of the filter output, the time instant of the start of inhale 257 may be identified. By identifying the maximum of the 7-tap filter output 269, the time instant of the start of exhale 259 may be identified. The smart delay time shifts the step impulses 203 generated from the running steps to a delayed version of the impulses and uses these delayed impulses to count inhale steps and exhale steps. By moving the impulses used to count steps sufficiently away in time from inhale-exhale transitions, counting errors may be reduced even in the presence of time perturbations. A smart delay may have a fixed delay value, a smart delay may have a programmable delay value, or a smart delay may have a delay value that is adaptive. Some users may be able to synchronize the start of inhale with a foot strike and the start of exhale with a foot strike. Some users may have difficulty synchronizing the start of inhale with a foot strike and the start of exhale with a foot strike. A smart delay may have a fixed component that is preset or user adjustable that may offset systematic errors due to differing delays in the breathing and movement signal paths, or systematic offsets due to the way a user performs patterned breathing.

With reference to FIG. 9, let us examine an implementation of an adaptive smart delay. First, identify the instantaneous average step to step time period StepAVG 237. StepAVG 237 may be generated by calculating the time from running step to running step and averaging this value or filtering this value. In an embodiment, StepAVG 237 may be determined by calculating the time difference between step impulses 203 and averaging these time differences or filtering these time differences. In an embodiment, the filter used to filter the time differences between step impulses 203 may be a lowpass filter. StepAVG 237 may be slowly varying, and will track the runner's speed. At 150 steps/minute, StepAVG over a few steps will be approximately 0.4 seconds. Second, take a fraction of StepAVG 237. In an embodiment, StepAVG 237 may be divided by two for a fraction of one-half In another embodiment, other fractions of StepAVG 237 may be used. And third, delay the step impulses 203 by a fraction of StepAVG 237, for example in the case where a fraction of one-half is used, delay by StepAVG/2 239. The result may be the delayed impulses 285a, 285b, and 285c will be approximately centered on the breathe in portion of cycle 258. Similarly, the step impulses 286a and 286b will be approximately centered on the breathe out portion of cycle 258. The proposed approach may provide robustness to small time perturbations of any of the breathe in-breathe out sensor 205 and the step impulses 203. A system implementing the proposed approach may ideally accommodate time perturbations less than StepAVG/2 239. The resulting inhale count 240 will be 3 241c and the resulting exhale count 242 will be 2 243b for a 3/2 measured breathing pattern. In FIG. 9, the time locations of step impulses 203 are shown as tic marks 233a-233h. And the time perturbation 247 associated with 233e is shown only on delayed impulse 286a.

In addition to use of a smart delay, the system may utilize averaging of the pattern measurements reported to the user to minimize the effect of time perturbations.

Figure 11A:
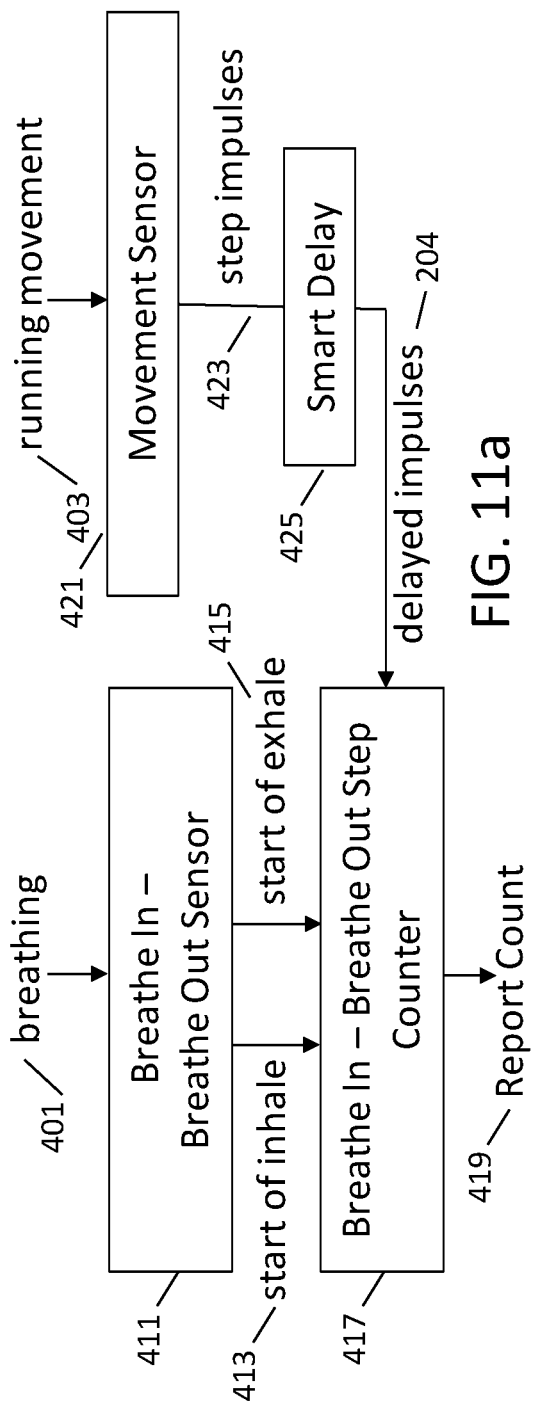
FIG. 11a illustrates a signal flow diagram for an embodiment of the breathing pattern identification algorithm that may be used for running.

An embodiment of the patterned breathing identification algorithm is illustrated in the flow diagram of FIG. 11a. For each of the flow diagrams presented in FIG. 11a, FIG. 11b, and FIG. 12, the wearable device is assumed to be placed on an appropriate location for sensing diaphragmatic breathing and running or walking step transients. Inputs to the flow diagram include the user's breathing 401 and the user's running (or walking) movement 403. Breathing 401 is input to the Breathe In-Breathe Out Sensor 411 which may output the start of inhale 413 and the start of exhale 415 signals. Other signals indicative of when a user is inhaling and exhaling may be output from the Breathe In-Breathe Out Sensor 411. The user's inhale period begins at the start of inhale 413 and ends at the start of exhale 415. The user's exhale period begins at the start of exhale 415 and ends at the start of inhale 413. The running movement 403 is input to the Movement Sensor 421, and the output of the Movement Sensor 421 may be step impulses 423 corresponding to foot strikes. These step impulses 423 may be input to a Smart Delay block 425 which may delay the step impulses 423 to create delayed impulses 204. Delayed impulses 204 may be used by the Breathe In-Breathe Out Step Counter 417 to count the number of steps taken during the inhale portion of the breathing cycle and count the number of steps taken during the exhale portion of the breathing cycle. An appropriate delay in the Smart Delay block 425 facilitates breathe in-breathe out step counting and minimizes sensitivity to small time perturbations. Sources of other system noise and impairments that may result in time perturbations include movement of the wearable on the body not related to breathing or running; movement due to factors such as belt elasticity, finite size of the sensor over only a portion of the region where contraction of the diaphragm may be detected; randomness in the runner's stride, objects on the running surface that the runner must avoid; and coughing or other natural body responses which may occur during running. Other sources of system noise and impairments may occur.

Figure 11B:
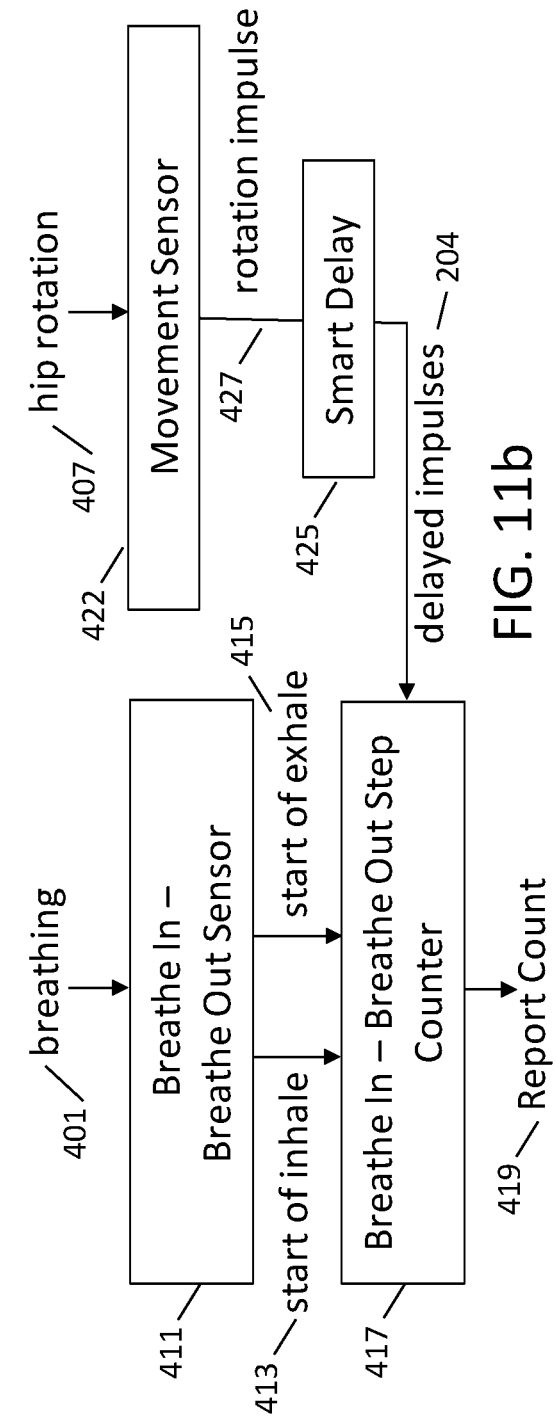
FIG. 11b illustrates a signal flow diagram for an embodiment of the breathing pattern identification algorithm that may be used for cycling.

Referring to FIG. 11b, the signal flow of FIG. 11a may be modified to identify patterned breathing for bicyclists and athletes in different sports. In cycling, with reference to the right foot, an entire 360 degree pedal rotation includes: a right foot thrust down on the right pedal with the right foot moving from the 12 o'clock position and ending at the 6 o'clock position while the left foot at the same time starts from the 6 o'clock position and ends at the 12 o'clock position; followed by a left foot thrust down on the left pedal with the left foot moving from the 12 o'clock position and ending at the 6 o'clock position while the right foot at the same time starts from the 6 o'clock position and returns to the 12 o'clock position. Counting half pedal rotations (12 o'clock to 6 o'clock movement of one foot) may be an appropriate parameter to count during breaths in and out in cycling. With reference to FIG. 11b, hip rotation 407 may be input to the Movement Sensor 421, with output of the Movement Sensor 421 rotation impulse 427 corresponding to a right leg cycling thrust, followed by a rotation impulse 427 corresponding to a left leg thrust, followed by a rotation impulse 427 corresponding to a right leg thrust and so forth. The rotation impulses 427 may be delayed by Smart Delay block 425 to generate delayed impulses 204. Delayed impulses 204 may be used by the Breathe In-Breathe Out Step Counter 417 to count the number of cycling half pedal rotations taken during the inhale portion of the breathing cycle and count the number of cycling half pedal rotations taken during the exhale portion of the breathing cycle. An appropriate delay in the Smart Delay block 425 facilitates breathe in-breathe out cycling half pedal rotation counting and minimizes sensitivity to small time perturbations. Sources of system noise and impairments that may result in time perturbations may be similar and analogous to those associated with running.

Figure 12:
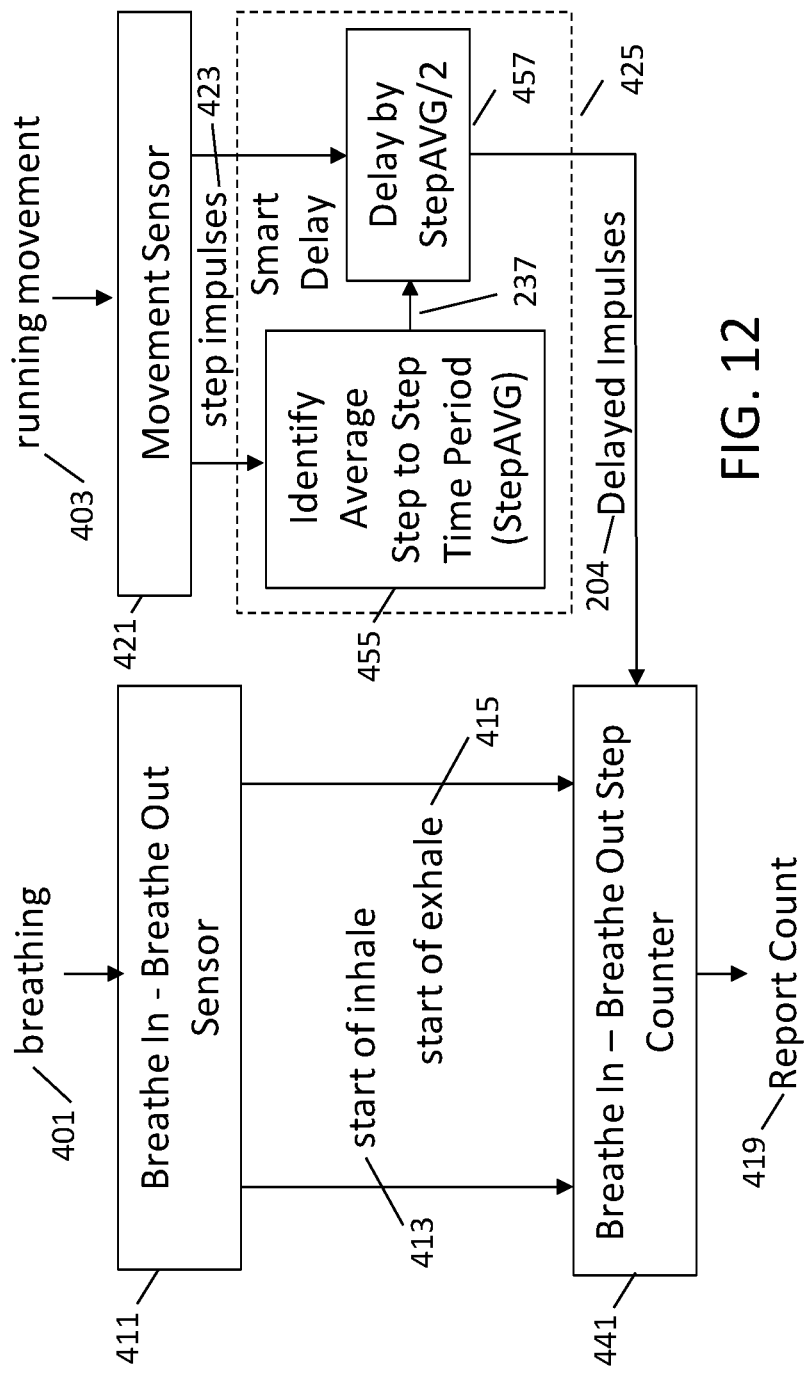
FIG. 12 illustrates a signal flow diagram for an embodiment of the breathing pattern identification algorithm that may be used for running showing an implementation of the Smart Delay.

With reference to FIG. 12, the signal flow diagram of FIG. 11a is expanded to illustrate more detail of the Smart Delay 425. This is one of many possible implementations of a smart delay block 425. This flow graph describes the algorithm presented in association with FIG. 9. Breathing 401 is input to the Breathe In-Breathe Out Sensor 411 and running movement 403 is input to the Movement Sensor 421. Breathe In-Breathe Out Sensor 411 and Movement Sensor 421 may include analog-to-digital conversion, filtering, automatic gain control, DC removal or modification, and other pre-processing prior to being operated on by the functional blocks. The output of the Breathe In-Breathe Out Sensor 411 block may be in different forms. In an embodiment, start of inhale in 413 and start of exhale 415 signals may be output that may be used to identify inhaling and exhaling. The running movement 403 is input to the Movement Sensor 421, and the output of the Movement Sensor 421 may be step impulses 423 corresponding to foot strikes. The Identify Average Step to Step Time Period (StepAVG) 455 generates StepAVG 237. In an embodiment, five samples may be used in the average. In another embodiment, 10 samples may be used in the average. In another embodiment, a different number of samples may be used in the average. In another embodiment StepAVG 237 may be generated by a filter. In an embodiment, the filter may include a lowpass filter. The value of StepAVG may be divided by two and used by the Delay StepAVG/2 block 457. With the delay from block 457 set to this value, delayed impulses 204 may be nearly centered on the inhale and exhale portions of a breathing cycle for robust step counting in the Breathe In-Breathe Out Step Counter 441 block. The output of block 441 is the count pattern 419 for the most recent inhale-exhale cycle. In an embodiment, there may be latency in generating the count pattern 419. In an embodiment, the count pattern 419 may be filtered before it is reported to the user.

The pattern of the number of steps for each in breath and number for each out breath can be represented by "X/Y" where X is the number of steps for each in breath and Y is the number of steps for each out breath. In an embodiment, the identified count pattern associated with a breathing cycle may be filtered or averaged together with identified breathing patterns in close time proximity of the breathing cycle before reporting the data to the user. For example, if a 3/2 pattern is measured for 3 breathing cycles, followed by a 4/1 pattern for one breathing cycle, and finally a 3/2 pattern for one breathing cycle, a 3/2 pattern may be reported in the location of the 4/1 pattern. A number of filtering methods may be used to conclude this. This result may be reported after the one cycle of latency associated with the final 3/2 pattern. In an embodiment, filtering or averaging may be used on the data when identifying the count pattern associated with a breathing cycle. In an embodiment, no averaging from breathing cycle to breathing cycle may be used. As an example of no cycle to cycle averaging, each breathing cycle may be evaluated in isolation. In an embodiment, both measured data using filtering or averaging and data with no cycle to cycle averaging may be reported to the user. In an embodiment, "rogue" data may be identified as having characteristics outside tolerances. In an embodiment, a breathing cycle containing rogue data may be discarded. Discarded data may reported to the user as discarded, or may not be reported to the user. Other signal processing methods and implementations may be utilized in the device and system for identifying, teaching, and improving the practice of using breathing patterns in running and walking.

The approach for using a smart delay 425 to delay step impulses 423 to generate delayed impulses 204 to define instants for counting inhale or exhale steps is one of many approaches that may be utilized to implement a patterned breathing identification algorithm. Critical sensor signals are relatively low in frequency compared with commonly used microprocessor clock rates. Running step rates are usually around 200 steps per minute or less for a distance runner and 300 steps per minute or less for a sprinter, while breathing cycle rates seldom exceed 100 Hz. Microprocessor clock rates are routinely in the hundreds of megahertz and may increase into the gigahertz range, and may depend on the immediate processing needs of the application. When rhythmic breathing is used, breathing patterns may not change often except when the runner is tiring and changing from a desired breathing pattern to ad hoc breathing. Since breathing patterns are generally slowly changing except in the case of ad hoc, latency from one to even a few breathing cycles in the reporting of a breathing pattern or average breathing pattern may be acceptable. These characteristics of the system and application including detected sensor signal bandwidths, the way breathing patterns may be used in practice, processing speeds of modern microprocessors, the ease and low cost of storing multiple breathing cycles in memory, and allowed latency in breathing pattern reporting may enable many different implementations of patterned breathing identification algorithms. Algorithms and portions of algorithms may be optimized for the identification of proper patterned breathing, known patterns that may occur when used by users learning patterned breathing, and unexpected patterns or anomalous patterns or data that may occur during patterned breathing or attempting patterned breathing. Since data reporting need not be immediate after each breathing cycle, data from one or more breathing cycles both before and after a particular breathing cycle may be used to increase the accuracy of identifying the breathing pattern that may have been used in the particular breathing cycle.

When aspects in the data from a particular breathing cycle appear inconsistent compared with breathing cycles in close time proximity, data from that particular breathing cycle may be discarded. For example, if a running step pattern is established with the time difference between steps changing by a small amount (for example 15% of the average time difference between steps) over several step cycles and suddenly, the measured time difference between steps changes by a relatively large amount (for example, greater than 40% of the average time difference between steps), the step with the large time difference change may be identified as a "rogue" step. The data associated with the breathing cycle including the rogue step may be discarded. Identifying anomalies such as a rogue step is an example of a potential advantage that may be taken by processing data from more than one breathing cycle at a time. Rhythmic breathing patterns (inhale and exhale) may tend to have more cycle to cycle variation than running steps, particularly for the student of patterned breathing. In a manner similar to identifying a rogue step, the observation of more than one breathing cycle of data may allow averaging to be utilized in the identification of breathing patterns. Such averaging may make the reported data less noisy and more reliable. To illustrate, suppose the start of inhale occurs periodically, for example, every two seconds. If the user is running with a 3/2 pattern, the start of each exhale should occur at roughly 1.2 seconds after the start of each inhale. The most likely errors in identifying a 3/2 pattern may be the identified patterns 2/3 or 4/1. These might occur if the start of each inhale moves ahead in time or is delayed in time by greater than 0.2 seconds. By averaging the time from each start of inhale to each start of exhale, the impact of a single advance or delay in the start of exhale greater than 0.2 seconds may be eliminated. These examples illustrate how anomalous data may be treated and in some cases corrected. Filtering as described in this example may actually introduce errors and therefore, in some embodiments may not be used.

In some applications, it may be desirable to store up to a few breathing cycles of data in electronic memory and utilize data from one or more breathing cycles to improve the accuracy of identifying breathing patterns in one or more breathing cycles. This may allow for better accuracy in measurements reported to the user. Filtering or averaging utilizes data from more than one breathing cycle. However, it may be limited to observation of specific qualities of the signals. For example, periods of non-breathing, little breathing, or holding one's breath may be identifiable by observing the breathe in-breathe out sensor output directly and identifying shapes, patterns, or specific qualities in the data. Pattern matching and identification may be facilitated by storing data for a few breathing cycles and evaluating or searching for anomalous patterns different from properly executed rhythmic breathing. When such patterns are identified, these behaviors may be flagged or reported to the user.

In non-movement or minimal movement applications, the Movement Sensor may not be used. In an embodiment, the Breathe In-Breathe Out Sensor may have a Breath Held output which may inform the system that the user may be holding their breath—not breathing in or not breathing out. This may be used as part of diaphragm training or in the teaching of specific breathing techniques. The Breath Held output may be active when the force or pressure on the breathe in-breathe out sensor is constant, not changing, or changing slowly.

Algorithms based on data taken from human activity with relatively simple sensors placed on a wearable device held in place by an elastic belt is fundamentally prone to error. This is especially true with a device that relies on direct contact to detect changes in incident pressure from the user's body. There are many parameters that may vary over time and conditions. There is limited opportunity for calibrations and there are numerous conditions for user error to occur. Furthermore, there may be assumptions that may be required to constrain algorithms to operate on somewhat well-behaved sets of data, or a fairly well defined and constrained models for device and system use. For example, we assume the runner is able to run symmetrically or nearly symmetrically so the time period from left foot strike to right foot strike is roughly the same as the time period from right foot strike to left foot strike. Further, we may assume the runner takes between 60 and 200 steps per minute. We may assume the runner's speed does not change quickly. There are other assumptions that may be required or parameters that may be required to be set for different algorithms. The focus of this presentation is to described how one of many possible algorithms might work and achieve at least a first order degree of robustness to cycle to cycle variations due to human movement and the use of fairly simple sensors. In light of these issues, when issues are addressed appropriately, an acceptable user experience may be possible.

Different filter structures and signal processing options may be utilized. In an embodiment, filters and other signal processing options may be selected or modified through the app. In an embodiment, adaptive filtering techniques are used where the tap weights of the filter are updated using an algorithm such as the LMS or least mean squares algorithm. In other embodiments, other adaptive filtering and adaptive signal processing techniques may be utilized.

In an embodiment, data regarding the runner's breathing pattern may be reported to the user. This data may be recorded inside the wearable or in the paired smart device to report breathing patterns at various points in a run. This may allow a runner to evaluate performance measures including speed, heart rate, steps per minute, and breathing pattern to develop and optimize strategies for performance optimization.

As described in the Incorporated Patent References, the device may include electronic memory to store data before, during, and after an athletic event such as a run. This data may be downloaded to an external device and may be combined with data from other sensing devices for presentation, evaluation, and study by an athlete or coach after the event. Data may also be transferred via a communication protocol to a smart device such as a smart watch during an event for real-time feedback, allowing the athlete to make modifications that may be in response to the received data during the event. The data provided by the device and system may include breathe in-breathe out sensor data and movement data. The data utilized may be raw data from sensors, partially processed data, or fully processed data with complete information for reporting to the user.

Figure 13:
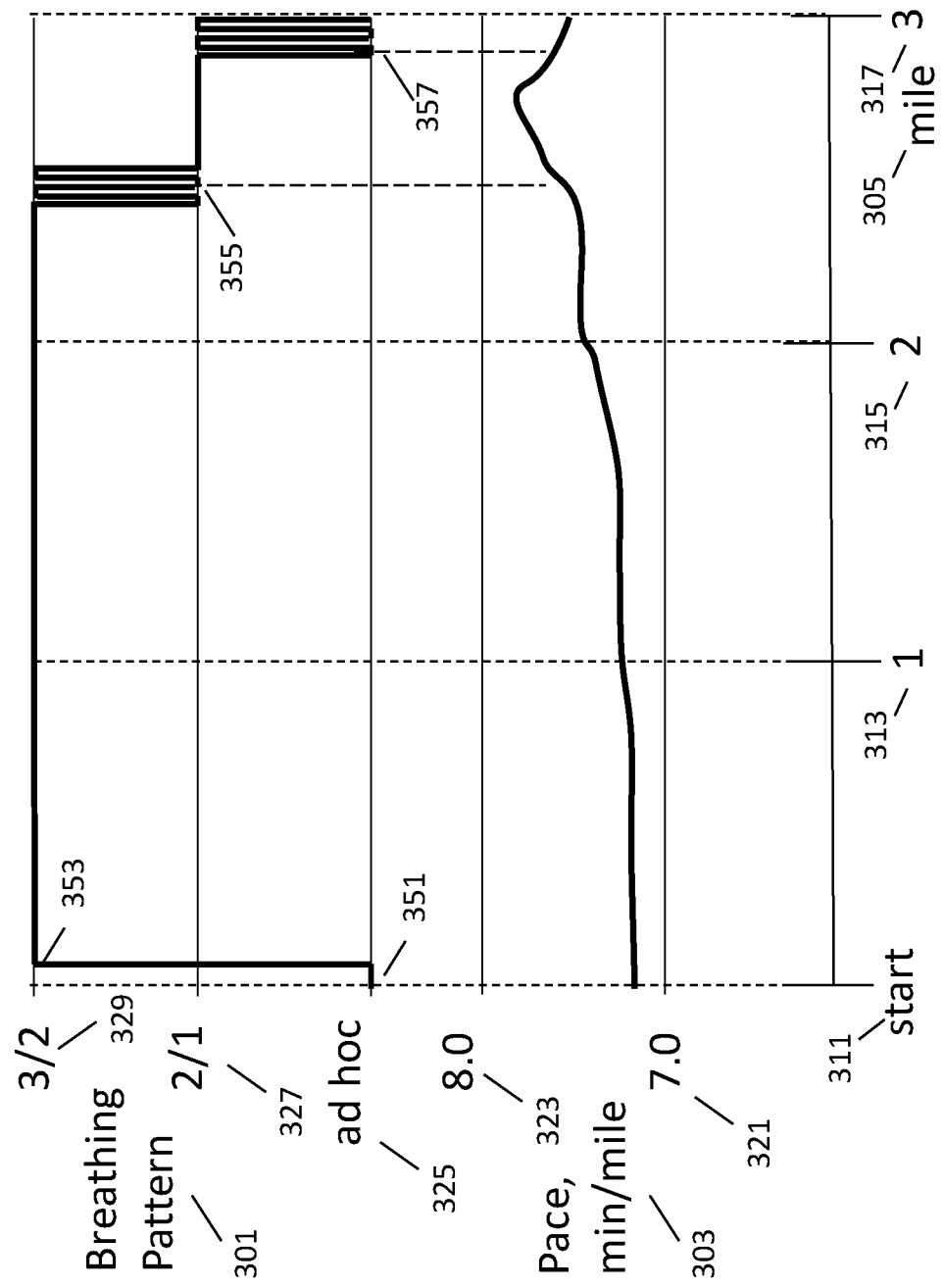
FIG. 13 illustrates a presentation of a simulated breathing pattern (top graph) over the duration of a 3 mile run with pace information (bottom graph). This presentation may be placed into the scene of an app.

With reference to FIG. 13, a runner runs 3 miles and her pace 303 is shown on the bottom graph as a function of distance 305. GPS may be used to track her distance 305. Alternatively, other sensors including accelerometers and gyros may be used to estimate distance 305. Her breathing pattern 301 is plotted on the top graph with the same x-axis of distance 305. The breathe in-breathe out sensor and movement sensor may be used and their outputs combined to estimate her breathing pattern 361. The breathing pattern designations chosen for the graph are ad hoc 325, 2/1 327, and 3/2 329. In this example, breathing patterns other than 3/2 329 or 2/1 327 are placed into the ad hoc 325 designation. In an embodiment, more than two specific breathing patterns may be identified. The runner begins at her highest pace and quickly changes from an ad hoc 325 breathing pattern to a 3/2 321 breathing pattern. She continues to run at her starting pace through mile 1 313, slowing a small amount during mile 2 315, and begins to slow down again at the end of mile 2 315. Near the middle 355 of mile 3, she slows down further and begins to change her breathing pattern from 3/2 329 to 2/1 327. Toward the end of her run, she begins increasing her pace 303 during her final kick to the end, while her breathing becomes ad hoc 325. Ad hoc 325 may include all patterns not identified in the graph 301 which may include 1/1.

Figure 14A:
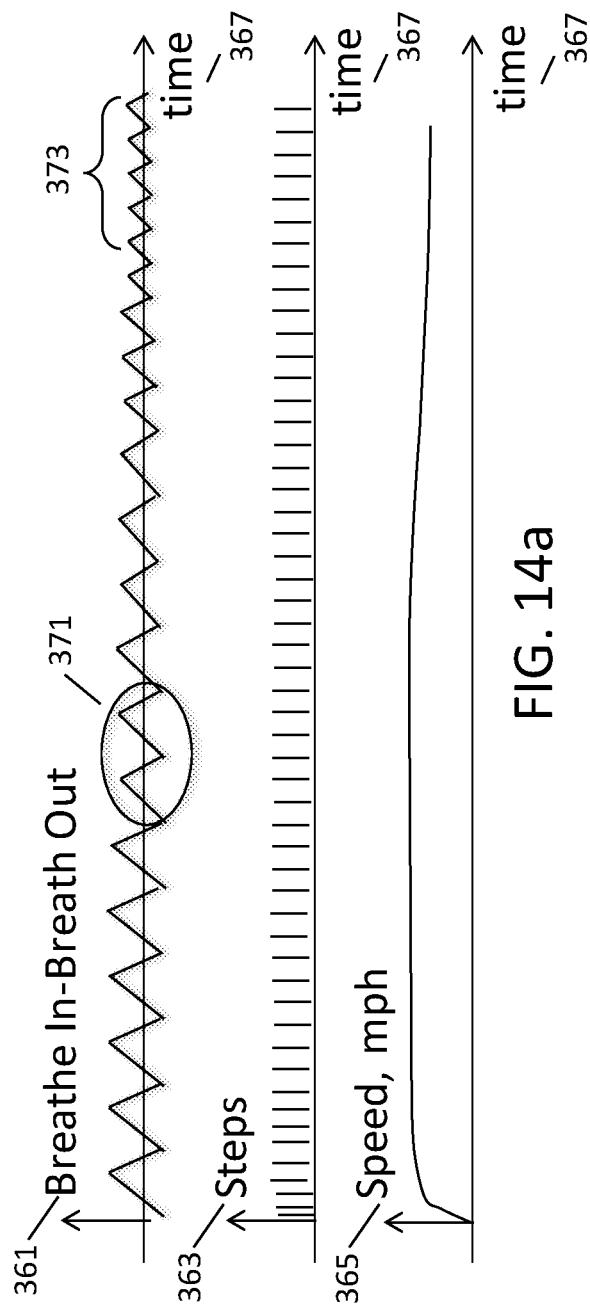
FIG. 14a illustrates a presentation of simulated data from an athlete running a 100 meter sprint. In the top graph is the breathe in-breathe out pattern. In the middle graph is the time position of each step. In the bottom graph is an estimate of the runner speed. This presentation may be placed into the scene of an app.
Figure 14B:
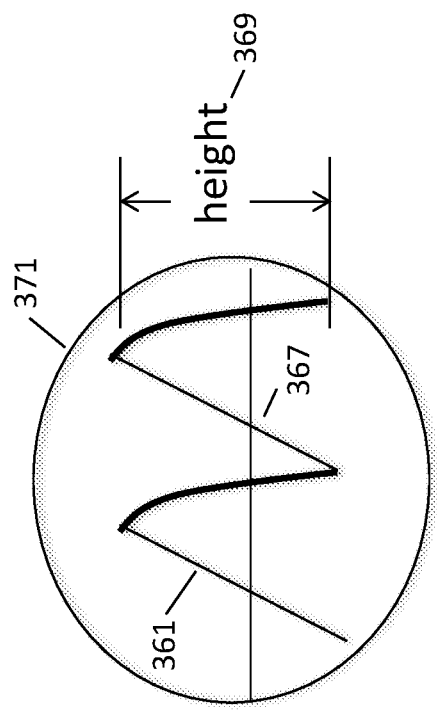
FIG. 14b illustrates a presentation of the zoomed in simulated data from a portion of the breathe in-breathe out pattern. This presentation may be placed into the scene of an app.

With reference to FIG. 14a, a sprinter's parameters including breathe in-breathe out 361, steps 363, and speed 365 are illustrated on graphs vs. time 367. The breathe in-breathe out sensor may be used to generate breathe in-breathe out signal 361 and the movement sensor may be used to generate steps signal 363. GPS may be used to track his speed 365. Alternatively, other sensors including accelerometers and gyros may be used to estimate speed 365. With reference to FIG. 14b, two cycles 371 of breathe in-breathe out 361 are shown at a larger scale than in FIG. 14a. The height 369 of the breathe in-breathe out 361 signal may be a measure of the depth of breathing in and out. The larger the height 369, the greater the volume of air may be moving into and out of the lungs. Toward the end of the sprint, the sprinter's 373 breathe in-breathe out 361 pattern becomes shallower as height 369 decreases and the frequency of his breathing increases. While he may have started with a 2/1 breathing pattern, he may finish with a 1/1 toward the end of his sprint 373.

Some sports emphasize a strong vigorous exhale to prepare the body for an similarly vigorous inhale. In some of these applications, the shape of the breathe in-breathe out signal 361 may be evaluated by the user to improve performance. Experienced athletes and coaches may identify specific details in the shape of the breathe in-breathe out signal 361 that may result in more effective breathing for a specific activity. Desirable details in the shape of the breathe in-breathe out signal 361 may be a part of a learning and teaching app or program and based on a user's breathing pattern that can be measured by the device and system, the app or program may provide feedback in real-time for improving the breathing technique of the user.

Heart rate monitoring is commonly utilized during running and walking. While a number of heart rate monitors have been integrated into watches, superior performance is achieved in heart rate monitors worn over the chest. The suggested location for heart rate monitors worn over the chest is very similar to the location shown in FIG. 1 for the wearable device for breathing pattern monitoring. In an embodiment, a heart rate monitor may be integrated into the wearable to enable simultaneous breathing pattern monitoring and feedback and heart rate monitoring. Implementations of the wearable that contain a buzzer or sound generator may allow the buzzer or sound generator to additionally be used to provide feedback to the user based on data received by the heart rate monitor. The addition of a heart rate monitor into the device may require a portion of the device to make direct contact with the skin.

In some applications, it may be desirable to simultaneously monitor both diaphragmatic patterned breathing and core muscle usage. In such cases, a system with two wearable devices may be utilized. One wearable may be worn over the celiac plexus to monitor diaphragmatic patterned breathing 105 (referring to FIG. 1) and the other wearable on a location to monitor the core muscles. For example, the side of the body may be used 115 between the ribs and hip bone (referring to FIG. 4c). In an embodiment, the wearables may be connected via a cable or a wireless connection to pass data from a first wearable to a second wearable where the second wearable my have a wireless connection to a smart device, PC, or other dedicated device. In an embodiment, both wearable devices may be connected via a wireless connection to a smart device, PC, or other dedicated device. Alternate approaches to implement a system with more than one wearable is described in the Incorporated Patent References. In an embodiment, the wearable device monitoring diaphragmatic patterned breathing may provide feedback via the user's smart device, PC, or other dedicated device. In an embodiment, the wearable device monitoring core engagement may provide feedback via the user's smart pad, smart watch, or other dedicated device. In an embodiment where it may be desirable to engage the core for long periods of time during a run, the wearable device monitoring core engagement may provide feedback by signaling when the user first engages their core and then providing short signals while the core remains engaged. The device may stop providing signals when the core stops being engaged. The signaling may be provided via the user's smart device, PC, or other dedicated device. The signaling may be provided via the device directly. The signal may be via a buzz provided by the device. The short signals provided while the core is engaged may be provided at user selected intervals. The short signals provided while the core is engaged may be periodic. For example, a short buzz may occur once every second. The user may use the periodic buzz to pace the steps of their run or walk.

An approach to running called chirunning may emphasize that the runner lean forward with an engaged core as a part of the running technique. Chirunning may have benefits of improved speed and reduced injuries. Chirunning may be combined with diaphragmatic breathing. The wearable device and system to promote diaphragmatic breathing and diaphragmatic patterned breathing may provide feedback to the user regarding the amount they are leaning forward during a run. In an embodiment, the device and system may report the number of degrees the user is leaning forward relative to a starting orientation. One or more of the sensors in the device including the accelerometer or gyro may be used to calculate a user's body orientation during the run. In some applications, a calibration may be performed where the user stands upright and then performs a calibration. The calibration may be performed during a reset of the device and system or a reset of portions of the device and system. In an embodiment, the user may reset the device and system by engaging the muscles under the force sensor or pressure sensor, and pressing the back of the device toward the body and then releasing shortly after. This may cause the detected pressure by the device to increase quickly and decrease quickly. This may be identified by the processor as a manual reset. In an embodiment, two or more press and release sequences may be used to indicate a reset. In an embodiment, other ways to initiate calibration may be used. The manual reset may be used to reset a number of parameters including the user's upright orientation. After calibrating, when the user leans forward during a run, their angle of forward lean which is their orientation relative to the initial upright orientation may be calculated. The processor may provide feedback when the angle of forward lean during running is out of a specified range. Alternatively, the processor may provide feedback when the angle of forward lean during running is within a specified range. In an embodiment, the range may be user programmable or adjustable. The device may also store this orientation data and report the data to the user after the run or event. Feedback may be provided via the device directly or via a smart device, PC, or other dedicated device. Other mechanisms may be used to reset or calibrate the device or system. For example, the device or system may be reset or calibrated when a button on the device is pressed or a button on a smart device, PC, or dedicated device running an app or program is pressed or touched. Signal processing techniques including filtering may be used to process orientation signals from the sensors to reduce noise, identify average orientation, or provide nuances in data reporting that may be important in specific applications.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing rhythmic breathing, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A method for outputting a measured breathing pattern of an athlete, comprising:
providing a wearable device having a force sensor having a sensor interface extending from a wearable device housing, the force sensor adapted for measuring expansion and compression of an abdomen of the athlete and a movement accelerometer sensor adapted for detecting step impulses for the athlete wherein the force sensor measures pressure increases when the athlete inhales and the force sensor measures pressure decreases when the athlete exhales, the movement accelerometer sensor detects steps of the athlete, the force sensor and the movement accelerometer sensor are in communication with a processor, and the force sensor, the movement accelerometer sensor, and the processor are in the wearable device housing;
transmitting breathing data during breathing cycles from the force sensor to the processor;
transmitting step impulse data from the movement accelerometer sensor to the processor;
calculating by the processor, the measured breathing pattern that is a count of a number of steps taken during each inhale portion of the breathing cycles while the force sensor measures the pressure increases and a count of the number of steps taken during each exhale portion of the breathing cycles while the force sensor measures the pressure decreases; and
displaying the measured breathing pattern on a visual display in communication with the processor or emitting the measured breathing pattern through an audio output device in communication with the processor.

2. The method of claim 1 wherein time instants used to count steps are determined by delaying step impulses.

3. The method of claim 2 wherein the delaying step impulses are a fixed delay value.

4. The method of claim 2 wherein the delaying step impulses are a programmable delay value.

5. The method of claim 1 wherein the measured breathing pattern is steps taken during each of the inhale portions of the breathing cycles or steps taken during each of the exhale portions of the breathing cycles.

6. A method for outputting a measured breathing pattern of an athlete, comprising:

provideing a wearable device having a force sensor having a sensor interface extending from a wearable device housing, the force sensor adapted for measuring expansion and compression of an abdomen of the athlete and a movement accelerometer sensor adapted for detecting step impulses for the athlete wherein the force sensor measures pressure increases when the athlete inhales and the force sensor measures pressure decreases when the athlete exhales, the force sensor and the movement accelerometer sensor are in communication with a processor, and the force sensor, the movement accelerometer sensor, and the processor are in the wearable device housing;

detecting hip rotations of the athlete by the movement accelerometer sensor;

transmitting hip rotation data from the movement accelerometer sensor to the processor;

detecting inhales and exhales of the athlete by the force sensor;

transmitting inhales and the exhales measurements during breathing cycles from the movement accelerometer sensor to the processor;

calculating by the processor, the hip rotations during each inhale portion of the breathing cycles while the force sensor measures the pressure increases and a count of a number of steps taken during each exhale portion of the breathing cycles the force sensor measures the pressure decreases;

calculating by the processor, the measured breathing pattern for the athlete that is a count of a number of hip rotations taken during each inhale portion of the breathing cycles while the force sensor measures the pressure increases and a count of the number of hip rotations taken during each exhale portion of the breathing cycles; and displaying the measured breathing pattern on a visual display in communication with the processor or emitting the measured breathing pattern through an audio output device in communication with the processor.

7. The method of claim 6 wherein time instants used to count steps are determined by delaying step impulses.

8. The method of claim 7 wherein the delaying step impulses are a fixed delay value.

9. The method of claim 7 wherein the delaying step impulses are a programmable delay value.

10. The method of claim 6 wherein the measured breathing pattern is steps taken during each of the inhale portions of the breathing cycles or steps taken during each of the exhale portions of the breathing cycles.

* * * * *